United States Patent [19]

Iyengar et al.

[11] Patent Number: 6,025,379
[45] Date of Patent: Feb. 15, 2000

[54] METHODS OF TREATING OR PREVENTING INTERSTITIAL CYSTITIS

[75] Inventors: Smriti Iyengar, Carmel; Mark A. Muhlhauser, Indianapolis, both of Ind.; Karl B. Thor, Morrisville, N.C.

[73] Assignee: Eli Lilly and Company, Indianapolis, Ind.

[21] Appl. No.: 09/125,956

[22] PCT Filed: Mar. 7, 1997

[86] PCT No.: PCT/US97/03895

§ 371 Date: Aug. 25, 1998

§ 102(e) Date: Aug. 25, 1998

[87] PCT Pub. No.: WO97/33873

PCT Pub. Date: Sep. 18, 1997

Related U.S. Application Data

[60] Provisional application No. 60/013,129, Mar. 11, 1996.

[51] Int. Cl.$^7$ .................................................. A61K 31/415
[52] U.S. Cl. ............................................ 514/395; 514/394
[58] Field of Search ...................................... 514/395, 394

[56] References Cited

U.S. PATENT DOCUMENTS 5,552,426   9/1996   Lunn ........................................ 514/394

OTHER PUBLICATIONS

The Journal of Urology, vol. 153, "Characterization of Tachykinin NK2 Receptors in Human Urinary Bladder," pp. 1688–1692 (1995).

*Primary Examiner*—Robert Gerstl
*Attorney, Agent, or Firm*—Elizabeth A. Dawalt; Paul J. Gaylo

[57] ABSTRACT

This invention provides methods for the treatment or prevention of interstitial cystitis or urethral syndrome in a mammal which comprise administering to a mammal in need thereof an effective amount of a substituted benzimidazole, or a pharmaceutically acceptable salt or solvate thereof.

3 Claims, No Drawings

METHODS OF TREATING OR PREVENTING INTERSTITIAL CYSTITIS

This application is a International 371 of PCT/US97/03895 filed Mar. 7, 1997. It also claims the benefit of U.S. Provisional Application No. 60/013,129 filed Mar. 11, 1996.

BACKGROUND OF THE INVENTION

Tachykinins are a family of peptides which share a common amidated carboxy terminal sequence. Substance P was the first peptide of this family to be isolated, although its purification and the determination of its primary sequence did not occur until the early 1970's.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides* 6 (Supplement 3):237–243 (1985) for a review of these discoveries.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

Tachykinins play a major role in mediating the sensation and transmission of pain or nociception, especially migraine headaches. see, e.g., S. L. Shepheard, et al., *British Journal of Pharmacology* 108:11–20 (1993); S. M. Moussaoui, et al., *European Journal of Pharmacology*, 238:421–424 (1993); and W. S. Lee, et al., *British Journal of Pharmacology*, 112:920–924 (1994).

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability.

Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in U.S. Pat. No. 5,328,927, issued Jul. 12, 1994; U.S. Pat. No. 5,360,820, issued Nov. 1, 1994; U.S. Pat. No. 5,344,830, issued Sep. 6, 1994; U.S. Pat. No. 5,331,089, issued Jul. 19, 1994; European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; and Patent Cooperation Treaty publication WO 93/011609, published Jan. 21, 1993.

Interstitial cystitis is a chronic debilitating inflammatory disorder of the bladder. The disease is most common in women ranging in age from about thirty to sixty with onset of the condition typically occurring at about forty years of age. It is characterized by a number of urinary difficulties, such as suprapubic pressure and pain, with bladder filling, urinary frequency, nocturia, dysuria, urgency and irritative voiding associated with morphological and histological changes in the bladder. The condition is characterized as "interstitial cystitis" because it is believed the condition does not affect the surface of the bladder, but instead involves the spaces between the cells, namely the interstices, in the lining of the bladder.

Urethral syndrome is a related painful voiding disorder of unknown etiology affecting women exhibiting many of the conditions set forth above.

As noted in U.S. Pat. No. 5,145,859, issued Sep. 8, 1992, the entire contents of which are herein incorporated by reference, there are a number of compounds proposed to treat these conditions, based on differing theories as to the etiology of interstitial cystitis and urethral syndrome. None of these treatment regimens has proven completely successful to date.

Because of the current dissatisfaction of the currently marketed treatments for interstitial cystitis within the affected population, there exists a need for a more efficacious and safe treatment.

SUMMARY OF THE INVENTION

This invention provides methods for the treatment or prevention of interstitial cystitis or urethral syndrome in a mammal which comprise administering to a mammal in need thereof an effective amount of a compound of Formula I

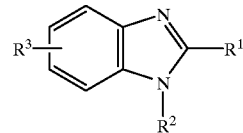

wherein:
  $R^1$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-,
    any one of which phenyl, naphthyl, heterocyclic, $C_3$–$C_8$ cycloalkyl, or unsaturated heterocyclic groups may be optionally substituted with one, two, or three moieties independently selected from group consisting of heterocyclic-($C_1$–$C_6$ alkylidenyl)-, unsaturated heterocyclic-($C_1$–$C_6$ alkylidenyl)-, hydroxy, halo, $C_1$–$C_6$ alkyl, $C_1$–$C_6$ alkoxy, trifluoromethyl, nitro, amino, cyano, $C_1$–$C_6$ alkylamino, and $C_1$–$C_6$ alkylthio;
  $R^2$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-(C$_1$–C$_6$ alkoxy)-, naphthyl-(C$_1$–C$_6$ alkoxy)-, heterocyclic-(C$_1$–C$_6$ alkoxy)-, or unsaturated heterocyclic-(C$_1$–C$_6$ alkoxy)-, any one of which phenyl, naphthyl, heterocyclic, C$_3$–C$_8$ cycloalkyl or unsaturated heterocyclic groups may be optionally substituted with one, two, or three moieties independenly selected from group consisting of phenyl-(C$_1$–C$_6$ alkylidenyl)-, naphthyl-(C$_1$–C$_6$ alkylidenyl)-, heterocyclic-(C$_1$–C$_6$ alkylidenyl)-, unsaturated heterocyclic-(C$_1$–C$_6$ alkylidenyl)-, phenyl-(C$_1$–C$_6$ alkoxy)-, naphthyl-(C$_1$–C$_6$ alkoxy)-, heterocyclic-(C$_1$–C$_6$ alkoxy)-, or unsaturated heterocyclic-(C$_1$–C$_6$ alkoxy)-, hydroxy, halo, C$_1$–C$_6$ alkyl, C$_1$–C$_6$ alkoxy, trifluoromethyl, nitro, amino, cyano, C$_1$–C$_6$ alkylamino, and C$_1$–C$_6$ alkylthio;

R$^3$ is hydrogen, nitro, C$_1$–C$_6$ alkanoyl, amino, C$_1$–C$_6$ alkyl, C$_1$–C$_6$ alkoxy, C$_3$–C$_8$ cycloalkyl, heterocyclic, unsaturated heterocyclic, halo, C$_1$–C$_6$ alkylthio, hydroxy-(C$_1$–C$_6$ alkylidenyl)-, hydroxy-(C$_1$–C$_6$ alkylidenyl)amino-, R$^4$R$^5$N-, R$^4$R$^5$N-(C$_1$–C$_6$ alkylidenyl)-, R$^4$R$^5$N-(C$_1$–C$_6$ alkoxy)-, hydroxy-(C$_1$–C$_6$ alkyl)-, heterocyclic-(C$_1$–C$_6$ alkoxy)-, amino (C$_1$–C$_6$ alkylidenyl)-, or trifluoromethyl, where R$^4$ and R$^5$ are independently selected from the group consisting of C$_1$–C$_6$ alkyl, C$_1$–C$_6$ alkoxy, C$_1$–C$_6$ alkanoyl, aryl, heterocyclic, unsaturated heterocyclic, aryl(C$_1$–C$_6$ alkylidenyl)-, heterocyclic (C$_1$–C$_6$ alkylidenyl)-, unsaturated heterocyclic (C$_1$–C$_6$ alkylidenyl)-, and hydrogen or R$^4$ and R$^5$ combine to form C$_3$–C$_8$ cycloalkyl, any one of which alkyl or alkoxy groups may be substituted with one or more halo, amino, or nitro, and any one of which aryl, unsaturated heterocyclic, or heterocyclic groups may be substituted with one, two, or three moieties independenly selected from group consisting of hydroxy, halo, C$_1$–C$_6$ alkyl, C$_1$–C$_6$ alkoxy, trifluoromethyl, nitro, amino, cyano, C$_3$–C$_8$ cycloalkyl, C$_1$–C$_6$ alkylamino, and C$_1$–C$_6$ alkylthio;

with the proviso that not more than one of R$^1$ and R$^2$ may be hydrogen;

or a pharmaceutically acceptable salt or solvate thereof, in combination with another analgesic whose primary mechanism of action is not as a tachykinin receptor antagonist.

DETAILED DESCRIPTION AND PREFERRED EMBODIMENTS

The terms and abbreviations used in the instant examples have their normal meanings unless otherwise designated. For example "°C" refers to degrees Celsius; "N" refers to normal or normality; "mol" refers to mole or moles; "mmol" refers to millimole or millimoles; "g" refers to gram or grams; "kg" refers to kilogram or kilograms; "L" refers to liter or liters; "ml" means milliliter or mililiters; "M" refers to molar or molarity; "MS" refers to mass spectrometry; and "NMR" refers to nuclear magnetic resonance spectroscopy.

As used herein, the term "C$_1$–C$_6$ alkyl" refers to straight or branched, monovalent, saturated aliphatic chains of 1 to 6 carbon atoms and includes, but is not limited to, methyl, ethyl, propyl, isopropyl, butyl, isobutyl, t-butyl, pentyl, isopentyl, and hexyl. The term "C$_1$–C$_6$ alkyl" includes within its definition the term "C$_1$–C$_3$ alkyl".

"Halo" represents chloro, fluoro, bromo or iodo.

The term "haloformate" as used herein refers to an ester of a haloformic acid, this compound having the formula

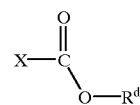

wherein X is halo, and R$^d$ is C$_1$–C$_6$ alkyl. Preferred haloformates are bromoformates and chloroformates. Especially preferred are chloroformates. Those haloformates wherein R$^d$ is C$_3$–C$_6$ alkyl are especially preferred. Most preferred is isobutylchloroformate.

The term "unsaturated heterocycle" represents a stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, and tetrahydroisoquolinyl.

"C$_1$–C$_6$ alkoxy" represents a straight or branched alkyl chain having from one to six carbon atoms attached to an oxygen atom. Typical C$_1$–C$_6$ alkoxy groups include methoxy, ethoxy, propoxy, isopropoxy, butoxy, t-butoxy, pentoxy and the like. The term "C$_1$–C$_6$ alkoxy" includes within its definition the term "C$_1$–C$_4$ alkoxy".

"C$_2$–C$_6$ alkanoyl" represents a straight or branched alkyl chain having from one to five carbon atoms attached to a carbonyl moiety. Typical C$_2$–C$_6$ alkanoyl groups include acetyl, propanoyl, isopropanoyl, butanoyl, t-butanoyl, pentanoyl, hexanoyl, 3-methylpentanoyl and the like.

"C$_3$–C$_8$ cycloalkyl" represents a saturated hydrocarbon ring structure containing from three to eight carbon atoms which is unsubstituted. Typical C$_3$–C$_8$ cycloalkyl groups include cyclopropyl, cyclopentyl, cyclohexyl, cycloheptyl, and cyclooctyl.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, C$_1$–C$_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl Further examples of these groups may be found in T. W. Greene and P. G. M. Wuts, PROTECTIVE GROUPS IN ORGANIC SYNTHESIS, (1991) at Chapter 3.

The compounds prepared in the processes of the present invention have an asymmetric center. As a consequence of this chiral center, the compounds produced in the present invention may occur as racemates, mixtures of enantiomers and as individual enantiomers, as well as diastereomers and mixtures of diastereomers. Processes for preparing such asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system is also used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

As noted supra, this invention includes methods employing the pharmaceutically acceptable salts of the compounds defined by Formula I. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses methods employing the pharmaceutically acceptable solvates of the compounds of Formula I. Many of the compounds of Formula I can combine with solvents such as water, methanol, ethanol and acetonitrile to form pharmaceutically acceptable solvates such as the corresponding hydrate, methanolate, ethanolate and acetonitrilate.

The term "treating" (or "treat") as used herein includes its generally accepted meaning which encompasses prohibiting, preventing, restraining, and slowing, stopping, or reversing progression, severity, or a resultant symptom. As such, the methods of this invention encompass both therapeutic and prophylactic administration.

The compounds of the present invention are derivatives of benzimidazole which are named and numbered according to the Ring Index, The American Chemical Society, as follows.

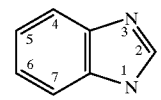

The preferred methods of this invention employ those compounds of Formula I wherein:
a) $R^1$ is phenyl, naphthyl, heterocyclic, unsubstituted heterocyclic, or substituted derivatives thereof;
b) $R^2$ is phenyl, heterocyclic, unsaturated heterocyclic, phenyl($C_1$–$C_6$ alkylidenyl)-, heterocyclic($C_1$–$C_6$ alkylidenyl)-, unsaturated heterocyclic($C_1$–$C_6$ alkylidenyl)-, or substituted derivatives thereof;
c) $R^3$ is $R^4R^5$N-($C_1$–$C_6$ alkylidenyl)-, $C_1$–$C_6$ alkanoyl,, $C_1$–$C_4$ alkoxy, imidazole, amino-($C_1$–$C_6$ alkylidenyl), hydroxy-($C_1$–$C_6$ alkylidenyl)amino-, heterocyclic-($C_1$–$C_6$ alkoxy)-, $R^4R^5$N-($C_1$–$C_6$ alkoxy)-, or hydroxy;
d) $R^3$ is at the 5 or 6 position of the benzimidazole.

The especially preferred methods of this invention employ those compounds of Formula I wherein:
a) $R^1$ is phenyl or naphthyl substituted with one or more electron donating, lipophilic substituents;
b) $R^2$ is substituted benzyl or substituted phenyl;
c) $R^3$ is $R^4R^5$N-($C_1$–$C_6$ alkylidenyl)-, heterocyclic-($C_1$–$C_6$ alkoxy)-, $R^4R^5$N-($C_1$–$C_6$ alkoxy)-, or unsaturated heterocyclic($C_1$–$C_6$ alkylidenyl)-; and
d) $R^3$ is at the 6 position of the benzimidazole.

The steps of this synthesis are described in European Patent Application Publication 694,535, to be published Jan. 31, 1996.

The compounds of Formula I can be prepared by processes known in the literature. See. e.g., G. W. H. Cheeseman and R. F. Cookson, THE CHEMISTRY OF THE HETEROCYCLIC COMPOUNDS, (A. Weissberger, et al., eds. 1979). The usual process for the preparation of the compounds of Formula I is by cyclization of an appropriately substituted o-phenylenediamine such as the one depicted in Formula III

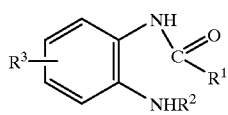

in a solvent or solvent mixture. It is generally preferred that the solvent or solvent mixture be heated, preferably to the boiling point of the solvent. Suitable solvents include ethanol, isopropanol, glacial acetic acid, benzene, toluene, chlorobenzene, glycol, ethylene glycol, dimethyl ether, diethyl ether, dimethylformamide, chloroform, ethyl acetate, and the like. It is generally preferred to add a condensation agent such as phosphorous oxychloride, thionyl chloride, p-toluenesulfonic acid, hydrochloric acid, sulfuric acid, phosphoric acid, polyphosphoric acid, phosphorous pentoxide, methanesulfonyl hydroxide, methanesulfonyl chloride, and the like. The cyclization reaction may also optionally be performed in the presence of a base such as sodium hydroxide, sodium mesylate, or potassium tert-butylate.

In those compounds in which $R^2$ is phenyl a derivative of N-phenyl-o-phenylenediamine was used as the starting material for the cyclization reaction. The examples if provide sufficient guidance in the preparation of those compounds of Formula I wherein $R^3$ is hydrogen.

Those compounds of Formula I wherein $R^3$ is not hydrogen, can be prepared by methods taught in the literature. For example, the compounds of this invention wherein $R^3$ is $C_2$–$C_6$ alkanoyl can be prepared from the appropriate keto o-phenylenediamine of the formula

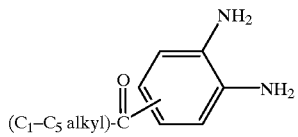

by methods known in the benzimidazole art such as the procedures described in U.S. Pat. No. 4,401,817, issued Aug. 30, 1983, which is herein incorporated by reference. The method of preparation involves the ammonolysis and reduction of a 4-halo-3-nitrophenyl ketone which is prepared by the Friedel-Crafts reaction of either a 4-halo-3-nitrobenzoyl chloride with an appropriate hydrocarbon or a halobenzene with an appropriate acid chloride followed by aromatic nitration.

Alternatively, the keto benzimidazole reactants can be prepared from acetanilide by a Friedel-Crafts acylation with the appropriate derivative of $C_2$–$C_6$ alkanoic acid. The resulting 4-keto acetanilide is nitrated to give a 2-nitro-4-ketoacetanilide. The acetanilide is hydrolyzed to give a 2-nitro-4-ketoaniline, which can then be catalytically hydrogenated to yield a 4-keto-o-phenylenediamine which can then be ring closed to provide the 5 or 6-substituted benzimidazole.

Those compounds of Formula III wherein $R^3$ is a substituted alkyl or alkylidenyl may be prepared by means of a Friedel-Crafts alkylation with the appropriate derivative of the $R^3$ moiety using standard procedures, usually employing an alkyl halide or an olefin in the presence of a catalyst such as aluminum chloride, aluminum bromide or another Lewis acid.

An alternative strategy for preparing those compounds of Formula I wherein $R^3$ is $C_1$–$C_6$ alkoxy, $R^4R^5N$-($C_1$–$C_6$ alkoxy)-, or heterocyclic-($C_1$–$C_6$ alkoxy)-, or a substituted derivative thereof, involves first reacting a 3-nitro-4-aminophenol with an acyl halide in the presence of a base

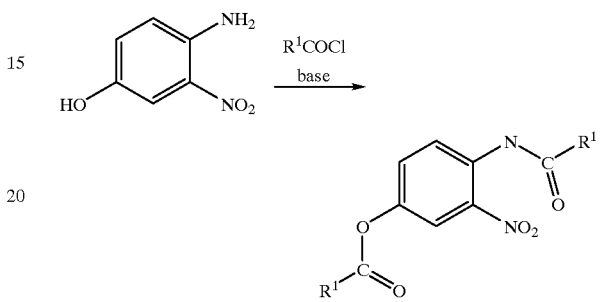

to get substitution of the primary amine as well as substitution of the hydroxy group, the ester moiety serving as a hydroxy-protecting group for subsequent reactions. In the next step of this synthesis the nitro group is then reduced to an amino group, usually by catalytic hydrogenation.

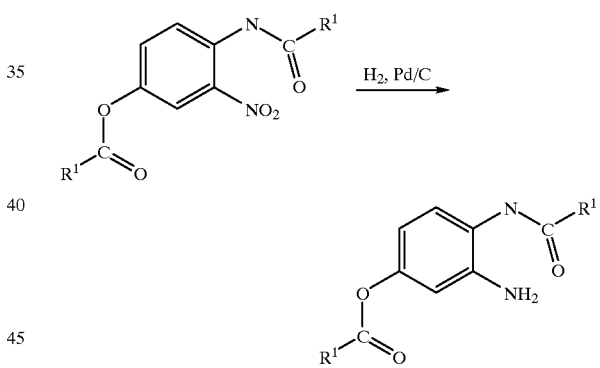

The primary amine of the above compound is then substituted, usually using an aldehyde, such as benzaldehyde or a substituted derivative thereof, followed by hydrogenation, if necessary. In an alternative embodiment, those compounds of Formula I in which $R^2$ is alkyl or substituted alkyl may be produced by alkylation of an aromatic amine with alkyl halide or tosylate, or the like, in the presence of a suitable base, such as trialkylamine, potassium carbonate, 1,8-diazabicyclo[5.4.0]undec-7-ene (DBU), and the like.

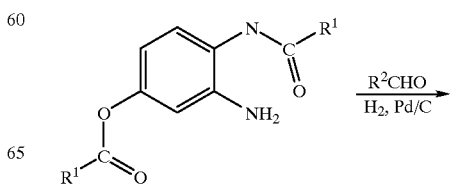

9
-continued

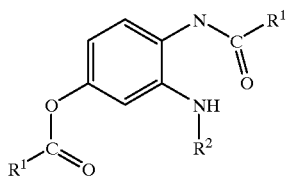

Cyclization of this substituted phenylenediamine is then performed as described supra, followed by cleavage of the ester group protecting the hydroxy group at the 6-position of the benzimidazole. Suitable cyclization catalysts include phosphorous oxychloride, thionyl chloride, phosphorous pentoxide, phosphorous pentachloride, and other like strong dehydrating agents.

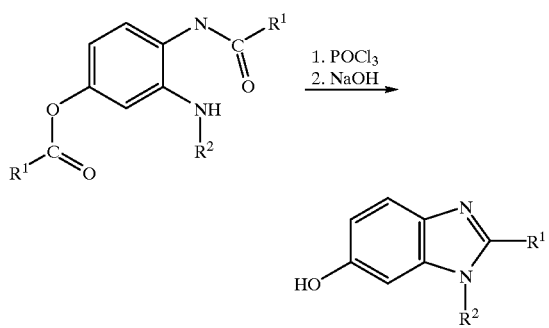

A preferred method of cleaving this ester is by incubation of the intermediate in a basic solution, such as 1N sodium hydroxide, or a weaker base such as potassium carbonate. The hydroxy group at the 6-position is then substituted using an alkyl or aryl halide, resulting in a compound of Formula I.

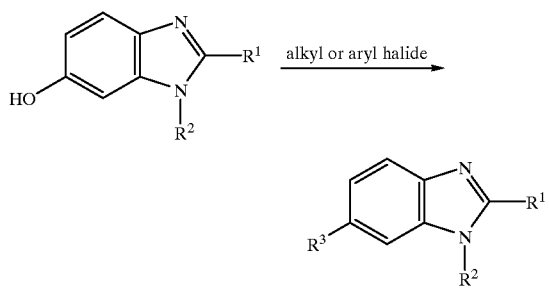

The skilled artisan understands that compounds of Formula I substituted at the 5-position of the benzimidazole can be prepared as described above by employing 3-amino-4-nitrophenol as the starting material instead of the 3-nitro-4-aminophenol shown supra.

Those compounds of Formula I wherein $R^2$ is alkyl or substituted alkyl may alternatively be prepared by the direct alkylation of a benzimidazole wherein the nitrogen at the 1-position is substituted with a hydrogen. This type of alkylation is usually performed by the reaction of the benzimidazole with an alkyl halide in the presence of a strong base, such as sodium hydride. This reaction is usually performed in a polar aprotic solvent, such as N,N-dimethylformamide, dimethyl sulfoxide, dimethylacetamide, hexamethylphosphoric triamide, and the like.

The following examples further illustrate the preparation of the compounds of Formula I. The examples are illustrative only and are not intended to limit the scope of the invention in any way. The designations "NMR", "IR", and "MS" in an example indicate that the nuclear magnetic resonance spectrum (NMR), the infrared absorption spectrum (IR), or the mass as determined by mass spectrometry (MS) were consistent with the desired compound.

EXAMPLE 1

Synthesis of 1,2-diphenylbenzimidazole

N-phenyl-o-phenylenediamine (10 mmol, 1.84 grams) was added to diethyl ether (100 ml) and stirred at room temperature as benzoyl chloride (10 mmol, 1.41 g) was added dropwise (a precipitate formed after about one half of the benzoyl chloride was added). After addition of the benzoyl chloride, the solution was stirred at room temperature for about 15 minutes. The reaction mixture was partitioned between aqueous sodium hydroxide and diethyl ether. The organic layer was removed and the aqueous layer was extracted with ethyl acetate (3×100 ml). The organic fractions were combined and dried over magnesium sulfate. The magnesium sulfate was filtered out and the solvent removed in vacuo to yield a red/brown solid (2.88 g, 99.8%) which was suitable for use in the cyclization reaction. NMR, mp 136–137° C.

A solution of the intermediate synthesized supra (2.5 g, 8.6 mmol) and phosphorous pentoxide/methanesulfonyl chloride (1:10) (30 ml) was heated at 100° C. for about one hour. The reaction mixture was then stirred with ice as 5N sodium hydroxide was added to raise the pH to 14. This moisture was then partitioned with ethyl acetate in a separation funnel. The ethyl acetate layer was removed and the aqueous layer was washed with ethyl acetate (3×100 ml). The organic layers were combined and dried over potassium carbonate overnight. The solution was filtered and the solvent removed in vacuo to yield 2.2 grams (94.6%) of crude product.

The product was purified by chromatography using a hexanes/ethyl acetate (4:1) solution as the eluent to yield 1.98 grams (85.2%) of the pure title product. NMR, MS 271(M+), mp 108–110° C.

Analysis for $C_{19}H_{14}N_2$: Theory: C, 84.42; H, 5.22; N, 10.36. Found: C, 84.72; H, 5.27; N, 10.35.

EXAMPLE 2

Synthesis of 1-phenyl-2-(4-methoxyphenyl)benzimidazole

A solution of N-phenyl-o-phenylenediamine (10 mmol, 1.84 g) in 100 ml diethyl ether was stirred at room temperature as p-anisoyl chloride (1 mmol, 1.71 g) was added dropwise. The resulting mixture was stirred at room temperature for about 96 hours. A precipitate formed before half of the anisoyl chloride/diethyl ether was added.

The resulting reaction mixture was partitioned with 1N sodium hydroxide and the organic layer separated. The aqueous layer was extracted with ethyl acetate (3×100 ml). The organic layers were combined and dried over potassium carbonate overnight, filtered, and the solvents were removed in vacuo. This yielded 3.57 grams of a dark brown crude product. Further purification could be performed by way of recrystallization from methylene chloride to yield a homogenous spot as determined by chromatography. mp 147–149° C.

A solution of the intermediate prepared supra (3.19 g, 10 mmol) in 35 ml phosphorous pentoxide/methanesulfonyl chloride (1:10) was stirred at 100° C. for about 2.5 hours. The resulting reaction mixture was poured over ice and stirred as aqueous sodium hydroxide was added. The final solution had a pH of 14. This solution was partitioned with ethyl acetate. The ethyl acetate layer was removed and the aqueous layer was extracted with ethyl acetate (3×100 ml). The organic layers were combined and washed with saturated sodium chloride. This was then dried over potassium carbonate, filtered, concentrated in vacuo to yield a brown/dark red crude product.

This crude product was purified by chromatography using hexanes/ethyl acetate (9:1) as eluent to yield 1.38 grams of the title product. NMR, MS 301(M+), mp 105–107° C.

Analysis for $C_{20}H_{16}N_2O$: Theory: C, 79.98; H, 5.37; N, 9.33. Found: C, 79.77; H, 5.38; N, 9.11.

EXAMPLE 3
Synthesis of 1-phenyl-2-phenylmethylbenzimidazole

The title intermediate was synthesized in substantial accordance with *Journal of Medicinal Chemistry* 18:319 (1975). A solution of N-phenyl-o-phenylenediamine (10 mmol, 1.84 g) and 2-ethoxy-1-ethoxycarbonyl-1,2-dihydroquinoline (12 mmol, 2.97 g) was stirred in methylene chloride (60 ml) at room temperature. Phenylacetic acid (10 mmol, 1.36 g) in methylene chloride (30 ml) was added via dropping funnel and stirred at room temperature over a drying tube overnight. The resulting reaction mixture was partitioned with 6N sodium hydroxide. The methylene chloride layer was removed and the aqueous layer was extracted with ethyl acetate (3×100). The organic fractions were combined, dried over potassium carbonate, filtered and the solvents were removed in vacuo to yield 5.28 grams of a dark red/brown crude product.

The crude product was recrystallized from ethyl acetate and then diethyl ether to yield a white crystalline product (1.77 g, 58.5%) of the title product. mp 108–110° C.

A portion of the intermediate synthesized supra (1.35 g, 4.5 mmol) and 30 ml of phosphorous pentoxide/methane sulfonyl hydroxide (1:10) were stirred at 100° C. for about 6 hours. The resulting reaction mixture was poured over ice and neutralized with aqueous sodium hydroxide (to pH 14). The aqueous layer was partitioned with ethyl acetate and separated. The aqueous layer was extracted with ethyl acetate (4×200 ml). The organic layers were combined, dried over potassium carbonate, and filtered. The solvent was removed in vacuo and the crude dark red/brown product was purified by chromatography using hexane/ethyl acetate (9:1) as the eluent. MS 285(M+), mp 106–108° C.

Analysis for $C_{20}H_{16}N_2O$: Theory: C, 84.48; H, 5.67; N, 9.85. Found: C, 84.75; H, 5.78; N, 9.93.

EXAMPLE 4
Synthesis of 1-phenyl-2-(3-chlorophenyl)benzimidazole

A solution of N-phenyl-o-phenylenediamine (1.84 g, 10 mmol) in diethyl ether (80 ml) was stirred at room temperature as 3-chlorobenzoylchloride (1.95 g, 11 mmol) in diethyl ether (30 ml) was added dropwise. Precipitate formed almost immediately after total addition of the 3-chlorobenzoylchloride. The resulting reaction mixture was stirred at room temperature for about 3 hours.

The reaction mixture was partitioned with aqueous sodium hydroxide. The organic layer was removed and the aqueous layer was extracted with ethyl acetate (3×120 ml). The organic layers were combined, dried over potassium carbonate, and filtered. The solvent was removed in vacuo to yield 3.5 grams of the desired intermediate.

Further purification could be performed using thin layer chromatography with hexanes/ethyl acetate (9:1) as the eluent. mp 133–134° C., NMR.

A solution of the intermediate prepared supra (2.50 g, 7.7 mmol) and 40 ml phosphorous pentoxide/methane sulfonyl hydroxide (1:10) was stirred at 100° C. for about 16 hours. This reaction mixture was then poured over ice and alkalinized with 5N sodium hydroxide (until pH=14). This aqueous solution was then extracted with ethyl acetate (5×150 ml). The organic layers were combined and dried over potassium carbonate, filtered, and concentrated in vacuo to yield 2.2 grams of crude red/brown product.

This crude product was further purified by chromatography using a hexanes/ethyl acetate (9:1) solution as the eluent. MS 305, 307, mp 107–109° C.

Analysis for $C_{19}H_{13}ClN_2$: Theory: C, 74.88; H, 4.30; N, 9.19. Found: C, 74.68; H, 4.47; N, 9.25.

EXAMPLE 5
Synthesis of 1-phenyl-2-(4-chlorophenyl)benzimidazole

A solution of N-phenyl-o-phenylenediamine (1.84 g, 10 mmol) in diethyl ether (80 ml) was stirred at room temperature as 4-chlorobenzoylchloride (1.95 g, 11 mmol) in diethyl ether (30 ml) was added dropwise. Precipitate formed almost immediately after total addition of the 4-chlorobenzoylchloride. After total addition of the 4-chlorobenzoylchloride, the resulting reaction mixture was stirred at room temperature for about 17 hours.

The reaction mixture was partitioned with 1N sodium hydroxide. The diethyl ether layer was removed and the aqueous layer extracted with ethyl acetate (4×150 ml). The organic layers were combined, dried over potassium carbonate, filtered, and concentrated in vacuo to yield 3.72 grams (>99%) of a dark red/brown solid. The crude product could be used as is or could be further purified. In the further purification the crude product was triturated in diethyl ether and filtered to yield an off-white solid. mp 169–171° C.

A portion of the intermediate synthesized above (crude, 2.84 g) was stirred in phosphorous pentoxide/methanesulfonyl hydroxide (1:10, 40 ml) at 100° C. for about 16 hours. The reaction mixture was poured over ice and alkalinized with 5N sodium hydroxide (pH=14). The aqueous layer was extracted with ethyl acetate (5×150 ml). The combined organic fractions were dried over potassium carbonate, filtered, and concentrated in vacuo to yield 2.52 grams of crude title product. Further purification could be accomplished by chromatography to yield a solid yellow crystal.

MS 305, 307, mp 139–141° C.

Analysis for $C_{19}H_{13}ClN_2$: Theory: C, 74.88; H, 4.30; N, 9.19. Found: C, 74.97; H, 4.33; N, 9.21.

EXAMPLE 6
Synthesis of 1-phenyl-2-(3-methoxyphenyl)benzimidazole

The titled intermediate was prepared essentially as described in Journal of Medicinal Chemistry, 18:319 (1975). A solution of N-phenyl-o-phenylenediamine (1.84 g, 10 mmol) and m-methoxybenzoic acid (1.52 g, 10 mmol) was stirred at room temperature in methylene chloride (80 ml). N-ethoxycarbonyl-2-ethoxy-1,2-dihydroquinoline (2.97 g) was added dropwise and the reaction was refluxed for about 16 hours. Additional N-ethoxycarbonyl-2-ethoxy-1,2-dihydroquinoline was added and the reaction was refluxed for an additional 18 hours.

The reaction mixture was partitioned with 1N sodium hydroxide. The organic layer (pH~14) was extracted with ethyl acetate (3×150 ml). The combined organic fractions were dried over potassium carbonate, filtered and concentrated in vacuo. Crude red oil was purified by chromatography using hexanes/ethyl acetate (9:1) as the eluent. White solid crystallized out of several fractions. mp 118–120° C.

A solution of the intermediate prepared above (1.08 g, 3.4 mmol) in chloroform (85 ml) was stirred at room temperature as phosphorous oxychloride (0.52 g, 3.4 mmol) in chloroform (35 ml) was added dropwise. The reaction mixture was then refluxed overnight.

The reaction mixture was partitioned with 1N sodium hydroxide. The organic layer was removed and the aqueous layer was extracted with chloroform (3×150 ml). The organic layers were combined, washed with a saturated sodium chloride solution, dried over potassium carbonate, filtered and the solvents were removed in vacuo to yield 1.18 grams (>99%).

The reaction product was further purified by chromatography using a hexanes/ethyl acetate (9:1) solution as eluent. MS 301(M$^+$), mp 110–111° C.

Analysis for $C_{20}H_{16}N_2O$: Theory: C, 79.98; H, 5.37; N, 9.33. Found: C, 79.72; H, 5.49; N, 9.39.

EXAMPLE 7

Synthesis of 1-phenyl-2-(4-nitrophenyl)benzimidazole 1-phenylamine-2-[(4-nitrophenyl)carbonylamino]benzene A solution of N-phenyl-o-phenylenediamine (1.84 g, 10 mmol) in diethyl ether (75 ml) was stirred at room temperature as 4-nitrobenzoylchloride (1.86 g, 10 mmol) in diethyl ether (40 ml) was added dropwise. A precipitate quickly formed. The reaction was stirred overnight.

The reaction mixture was partitioned with 1N sodium hydroxide and the organic layer removed. The aqueous layer (pH~14) was extracted with ethyl acetate (3×100 ml). The organic layers were combined, washed with saturated sodium chloride, dried over potassium carbonate, filtered and concentrated in vacuo.

The resulting crude product was triturated with diethyl ether and filtered to yield 2.48 grams of an orange/brown product was homogenous by chromatography. mp 169–171° C.

A solution of the above-prepared intermediate (2.48 g, 7.4 mmol) in chloroform (80 ml) was stirred at room temperature as phosphorous oxychloride (1.13 g, 7.4 mmol) in chloroform (35 ml) was added dropwise. After constant addition the reaction mixture was refluxed overnight.

The reaction mixture was cooled and partitioned with 1 N sodium hydroxide (pH~14). The organic layer was separated and the aqueous layer was extracted with chloroform (3×100 ml). The organic layers were combined, washed with saturated sodium chloride solution, dried over potassium carbonate, filtered, and the solvents were removed in vacuo to yield 2.50 grams of a yellow/green solid. The reaction product was purified by chromatography using a hexanes/ethyl acetate (4:1) solution as eluent. MS 316(M$^+$), mp 175–177° C.

Analysis for $C_{19}H_{13}N_3O_2$: Theory: C, 72.37; H, 4.15; N, 13.33. Found: C, 72.67; H, 4.16; N, 13.30.

EXAMPLE 8

Synthesis of 1-(4-chlorophenyl)-2-phenylbenzimidazole

A solution of N-(4-chlorophenyl)-1,2-phenylenediamine (2.19 g, 10 mmol) in diethyl ether (75 ml) was stirred at room temperature as benzoyl chloride (1.41 g, 10 mmol) in diethyl ether (30 ml) was added dropwise. A precipitate quickly formed. The reaction mixture was stirred overnight and partitioned with 1N sodium hydroxide.

The organic layer was removed and the aqueous layer (pH~14) was extracted with ethyl acetate (3×150 ml). The organic layers were combined, washed with saturated sodium chloride, dried over potassium carbonate, filtered and removed in vacuo. The crude product was triturated in diethyl ether to yield 1.84 grams (57%) of a white solid which was chromatographically homogenous. mp 158–160° C.

A solution of the intermediate prepared supra (0.33 g, 7.2 mmol) in chloroform (80 ml) was stirred at room temperature as phosphorous oxychloride (1.10 g, 7.2 mmol) in chloroform (30 ml) was added dropwise. After the addition was complete the reaction mixture was refluxed overnight. The reaction mixture was alkalinized to pH=14 with 1N sodium hydroxide and separated.

The aqueous layer was extracted with chloroform (3×10 ml). The organic layers were combined, washed with a saturated sodium chloride, dried over potassium carbonate, filtered, and the solvents were removed in vacuo to yield 2.45 grams of a red/brown oil which solidified upon setting at room temperature. The product was purified by chromatography using a hexanes/ethyl acetate (4:1) as eluent. MS 305, 307, mp 122–123° C.

Analysis for $C_{19}H_{13}ClN_2$: Theory: C, 74.88; H, 4.30; N, 9.19. Found: C, 75.18; H, 4.30; N, 9.15.

EXAMPLE 9

Synthesis of 1-phenyl-2-(3-trifluoromethylphenyl)-benzimidazole

A solution of N-phenyl-o-phenylenediamine (1.84 g, 10 mmol) in diethyl ether (80 ml) was stirred at room temperature as m-trifluorormethylbenzoyl chloride (2.09 g, 10 mmol) in diethyl ether (30 ml) was added dropwise. The reaction mixture was stirred overnight.

The reaction mixture was partitioned with 1N sodium hydroxide (pH~14) and the organic layer removed. The aqueous layer was extracted with ethyl acetate (3×100 ml). The organic layers were combined, washed with a saturated sodium chloride solution, dried over potassium carbonate, filtered, and the solvents were removed in vacuo to yield a dark red/brown oil which solidified upon standing at room temperature. The reaction product was purified by chromatography using a hexanes/ethyl acetate (4:1) solution as eluent.

A solution of the intermediate prepared above (3.20 g, 9.0 mmol) in chloroform (85 ml) was stirred at room temperature as phosphorous oxychloride (1.78 g, 9 mmol) in chloroform (35 ml) was added dropwise. The reaction mixture was refluxed overnight.

The reaction mixture was partitioned with 1N sodium hydroxide. The organic layer was removed and the aqueous layer was extracted with chloroform (3×150 ml). The organic layers were combined, washed with a saturated sodium chloride solution, dried over potassium carbonate, filtered, and the solvents were removed in vacuo to yield 3.00 grams of a yellow/brown oil which solidified upon standing.

The reaction product was further purified by chromatography using a hexanes/ethyl acetate (9:1 to 4:1) solution as eluent, yielding 1.89 grams (62%) of a light yellow solid. MS 339(M$^+$), mp 99–101° C.

Analysis for $C_{20}H_{13}F_3N_2$: Theory: C, 71.00; H, 3.87; N, 8.28. Found: C, 71.21; H, 4.07; N, 8.42.

EXAMPLE 10

Synthesis of 1-phenyl-2-(3-nitrophenyl)benzimidazole

A solution of N-phenyl-o-phenylenediamine (1.84 g, 10 mmol) in diethyl ether (80 ml) was stirred at room temperature as 3-nitrobenzoyl chloride (1.86 g, 10 mmol) in diethyl ether (30 ml) was added dropwise. The reaction mixture was stirred overnight at room temperature.

The reaction mixture was partitioned with 1N sodium hydroxide. The organic layer was removed and the aqueous layer was extracted with ethyl acetate (3×100 ml). The organic layers were combined, washed with a saturated sodium chloride solution, dried over potassium carbonate, filtered, and the solvents were removed in vacuo.

The product was purified by trituration with diethyl ether to yield 2.19 g (65.7%) of a yellow solid. mp 127–129° C.

A solution of the intermediate prepared above (2.9 g, 8.7 mmol) in chloroform (85 ml) was stirred at room temperature was phosphorous oxychloride (in 35 ml chloroform) was added dropwise. The reaction mixture was then refluxed overnight.

The reaction mixture was partitioned with 1N sodium hydroxide and the organic layer was removed. The aqueous layer was extracted with chloroform (3×120 ml). The organic fractions were combined, washed with a saturated sodium chloride solution, dried over potassium carbonate, filtered, and the solvents were removed in vacuo to yield 2.50 grams of a brown/green solid.

The reaction product was further purified using thin layer chromatography with a hexanes/ethyl acetate (9:1 to 4:1) solution as eluent. MS 316(M$^+$), mp 166–168° C.

Analysis for $C_{19}H_{13}N_3O_2$: Theory: C, 72.37; H, 4.16; N, 13.33. Found: C, 72.54; H, 4.27; N, 13.55.

EXAMPLE 11
Synthesis of 1-(4-chlorophenyl)-2-(4-chlorophenyl)-benzimidazole

A solution of N-(4chlorophenyl)-1,2-phenylenediamine (2.19 g, 10 mmol) in diethyl ether (85 ml) was stirred at room temperature as 4-chlorobenzoyl chloride (1.75 g, 10 mmol) in diethyl ether (35 ml) was added dropwise. The reaction mixture was stirred overnight at room temperature.

The reaction mixture was partitioned with 1N sodium hydroxide. The organic layer was removed and the aqueous layer (pH~14) was extracted with ethyl acetate (3×100 ml). The organic fractions were combined, washed with a saturated sodium chloride solution, dried over potassium carbonate, filtered, and the solvents were removed in vacuo to yield a crude red/brown solid.

The reaction product was purified by trituration with diethyl ether to yield 2.91 grams (81.5%) of an off-white solid which was chromatographically homogeneous. mp 180–181° C.

A solution of the intermediate prepared above (3.16 g, 8.8 mmol) in chloroform (90 ml) was stirred at room temperature as phosphorous oxychloride (1.36 g, 8.8 mmol) in chloroform (35 ml) was added dropwise. The reaction mixture was then refluxed overnight.

The mixture was partitioned with 1N sodium hydroxide and the organic layer was removed. The aqueous fraction was extracted with chloroform (3×150 ml). The organic layers were combined, washed with a saturated sodium chloride solution, dried over potassium carbonate, filtered, and the solvents were removed in vacuo to yield 2.83 grams of a gray/brown solid.

The reaction product was further purified by chromatography to yield 2.31 grams (77%) of a light pink solid. MS 339, 341, mp 162–164° C.

Analysis for $C_{19}H_{12}Cl_2N_2$: Theory: C, 67.27; H, 3.57; N, 8.30. Found: C, 67.45; H, 3.72; N, 8.36.

EXAMPLE 12
Synthesis of 1-phenyl-2-(4-trifluoromethylphenyl)-benzimidazole

A solution of N-phenyl-o-phenylenediamine (1.84 g, 10 mmol) in diethyl ether (85 ml) was stirred at room temperature as 4-(trifluoromethyl)benzoyl chloride (2.09 g, 10 mmol) in diethyl ether (30 ml) was added dropwise. The reaction mixture was stirred overnight at room temperature.

The reaction mixture was partitioned with 1N sodium hydroxide. The organic layer was removed and the aqueous layer extracted with ethyl acetate (3×100 ml). The organic layers were combined, washed with a sodium chloride solution, dried over potassium carbonate, filtered, and the solvents were removed in vacuo to yield a brown/black solid.

The crude product was triturated with diethyl ether and vacuum filtered to yield 2.56 grams (72%) of a yellow solid which was homogeneous on thin layer chromatography. mp 143–145° C.

A solution of the intermediate prepared above (3.25 g, 9.1 mmol) in chloroform (85 ml) was stirred at room temperature as phosphorous oxychloride in chloroform (35 ml) was added dropwise. The reaction mixture was partitioned with 1N sodium hydroxide.

The organic layer was removed and the aqueous layer was extracted with chloroform (3×150 ml). The organic layers were combined, washed with a saturated sodium chloride solution, dried over potassium carbonate, filtered, and the solvents were removed in vacuo to yield a red/brown oil which solidified upon standing.

The reaction product was further purified by chromatography using a hexanes/ethyl acetate (9:1 to 4:1) solution as eluent. Yield: 2.39 grams (77.6%) of a light yellow solid MS 339(M$^+$), mp 133–135° C.

Analysis for $C_{20}H_{13}F_3N_2$: Theory: C, 71.00; H, 3.87; N, 8.28. Found: C, 71.28; H, 3.99; N, 8.46.

EXAMPLE 13
Synthesis of 1-phenyl-2-(2-naphthyl)benzimidazole

A solution of N-phenyl-o-phenylenediamine (1.84 g, 10 mmol) was stirred at room temperature in diethyl ether (85 ml) as naphthoyl chloride (10 mmol, 1.91 g) in diethyl ether (35 ml) was added dropwise. The reaction mixture was stirred overnight at room temperature.

The reaction mixture was alkalinized with 1N sodium hydroxide. The organic layer was removed. The aqueous layer pH~14) was extracted with ethyl acetate (3×100 ml). The organic fractions were combined, washed with a saturated sodium chloride solution, dried over potassium carbonate, filtered, and the solvents were removed in vacuo to yield a red/brown solid (3.91 g, >99%).

The solid was triturated with diethyl ether and the remaining solid was collected by vacuum filtration. The reaction product was further purified by chromatography using a hexanes/ethyl acetate (9:1) solution as eluent. mp 147–149° C.

A solution of the intermediate prepared above (2.4 g, 7.1 mmol) in chloroform (85 ml) was stirred at room temperature as phosphorous oxychloride (1.1 g, 7.1 mmol) in chloroform (35 ml) was added dropwise. After the addition the reaction mixture was refluxed overnight.

The reaction mixture was alkalinized with 1N sodium hydroxide. The organic layer was removed and the aqueous layer was extracted with chloroform (3×150 ml). The organic layers were combined, washed with a saturated sodium chloride solution, dried over potassium carbonate, filtered, and the solvents were removed in vacuo to yield 2.38 grams (>99%) of a brown solid.

The reaction product was further purified by chromatography using a hexanes/ethyl acetate solution as the eluent to yield 1.91 grams (84%) of a light yellow solid. MS 321(M$^+$), mp 169–170° C.

Analysis for $C_{23}H_{16}N_2$: Theory: C, 86.22; H, 5.03; N, 8.04. Found: C, 86.21; H, 5.24; N, 8.61.

EXAMPLE 14
Synthesis of 1-phenyl-2-(3,5-dimethoxyphenyl)benzimidazole

A solution of N-phenyl-o-phenylenediamine (1.84 g, 10 mmol) in diethyl ether (85 ml) was stirred at room temperature as 3,5-dimethylbenzoyl chloride (2.00 g, 1.84 mmol) in diethyl ether (35 ml) was added dropwise. The reaction mixture was stirred at room temperature overnight.

The reaction mixture was alkalinized with 1N sodium hydroxide and the organic layer was removed The aqueous layer was extracted with ethyl acetate (3×100 ml). The organic layers were combined, washed with a saturated sodium chloride solution, dried over potassium carbonate, filtered, and the solvents were removed in vacuo to yield 3.46 grams of a red/brown oil which solidified upon standing.

Further purification of the title intermediate was achieved by chromatography. mp 107–109° C.

A solution of the crude product of the reaction above (2.3 g, 6.6 mmol) in chloroform (85 ml) was stirred at room temperature as phosphorous oxychloride (1.01 g, 6.6 mmol) in chloroform (25 ml) was added dropwise. The reaction mixture was then refluxed overnight.

The reaction mixture was alkalinized with 1N sodium hydroxide. The organic layer was removed and the aqueous layer was extracted with methylene chloride (3×100 ml). The organic layers were combined, washed with saturated sodium chloride solution, dried over potassium carbonate, filtered, and the solvents were removed in vacuo to yield a red/brown oil which solidified upon standing.

Further purification of the reaction product was accomplished by chromatography, employing a hexanes/ethyl acetate mixture as the eluent to yield 1.91 grams (87.6%) of a light yellow solid.

MS 331($M^+$), mp 98–99° C.

Analysis for $C_{21}H_{18}N_2O_2$: Theory: C, 76.34; H, 5.49; N, 8.48. Found: C, 76.17; H, 5.60; N, 8.51.

EXAMPLE 15

Synthesis of 1-phenyl-2-(3,4-dimethoxyphenyl) benzimidazole

A solution of N-phenyl-o-phenylenediamine (1.84 g, 10 mmol) in diethyl ether (85 ml) was stirred at room temperature as 3,4-dimethoxybenzoyl chloride (2.01 g, 10 mmol) in 40 ml of diethyl ether was added dropwise. The reaction mixture was then stirred overnight at room temperature.

The reaction mixture was then alkalinized with 1N sodium hydroxide. The organic layer was removed and the aqueous layer was extracted with diethyl ether (3×150 ml). The organic fractions were combined, washed with a saturated sodium chloride solution, dried over potassium carbonate, filtered, and the solvents were removed in vacuo to yield 3.11 grams.

This intermediate was further purified by chromatography using a hexanes/ethyl acetate solution as the eluent, followed by trituration with hexanes to yield a white crystalline solid. mp 159–160° C.

A solution of the intermediate prepared supra (3.11 g, 8.9 mmol) in chloroform (30 ml) was stirred at room temperature as phosphorous oxychloride (1.40 g, 9 mmol) in chloroform (30 ml) was added dropwise. The reaction mixture was then refluxed overnight. The reaction mixture was partitioned with 1N sodium hydroxide.

The organic fraction was removed and the aqueous phase was extracted with methylene chloride (3×150 ml). The organic fractions were combined, washed with saturated sodium chloride solution, dried over potassium carbonate, filtered, and the solvents were removed in vacuo to yield a brown oil which solidified upon standing.

The crude product was partitioned between 1N hydrochloric acid and a hexanes/ethyl acetate (1:1) solution. The aqueous layer was removed and the organic layer was extracted with 1N hydrochloric acid (3×100 ml). The aqueous fractions were combined and alkalinized to pH 14 with sodium hydroxide. This basified solution was extracted with ethyl acetate (5×100 ml). The organic layers were combined, washed with a saturated sodium chloride solution, dried over potassium carbonate, filtered, and the solvents were removed in vacuo to yield 1.70 grams (57.8%) of a pink solid. MS 331($M^+$), mp 114–115° C.

Analysis for $C_{21}H_{18}N_2O_2$: Theory: C, 76.34; H, 5.49; N, 8.48. Found: C, 76.31; H, 5.63; N, 8.53.

EXAMPLE 16

Synthesis of 1-phenyl-2-(3,4,5-trimethoxyphenyl)-benzimidazole

A solution of N-phenyl-o-phenylenediamine (1.84 g, 10 mmol) in diethyl ether (90 ml) was stirred at room temperature as 3,4,5-trimethoxybenzoyl chloride (2.31 g, 10 mmol) in diethyl ether (40 ml) was added dropwise. The reaction mixture was then stirred overnight at room temperature. The solvents were then removed in vacuo leaving N-[(3,4,5-trimethoxyphenyl)carbonyl)-N'-phenyl-phenylenediamine.

The crude intermediate (3.6 g, 9.5 mmol) in chloroform (100 ml) was stirred at room temperature as phosphorous oxychloride (1.5 g, 9.5 mmol) in chloroform (20 ml) was added dropwise. The reaction mixture was then stirred at room temperature for about 72 hours.

The reaction mixture was partitioned between 1N hydrochloric acid and ethyl acetate. The organic phase was discarded and the aqueous phase was alkalinized with 1N sodium hydroxide. The aqueous solution was then extracted with ethyl acetate (3×100 ml). The organic fractions were combined and dried over potassium carbonate. The solvents were removed in vacuo to yield the title product as a white solid (2.08 g, 61%). MS 361($M^+$), mp 139–141° C.

Analysis for $C_{22}H_{20}N_2O_3$: Theory: C, 73.32; H, 5.59; N, 7.77. Found: C, 73.17; H, 5.71; N, 7.72.

EXAMPLE 17

Synthesis of 1-(4-chlorophenyl)-2-(4-methoxyphenyl)-benzimidazole

A solution of N-(4-chlorophenyl)-1,2-phenylenediamine (2.13 g, 10 mmol) in diethyl ether (90 ml) was stirred at room temperature as p-anisoyl chloride (1.71 g, 10 mmol) in diethyl ether (45 ml) was added dropwise. The mixture was stirred overnight at room temperature.

The reaction mixture was partitioned with 1N sodium hydroxide. The organic layer was removed and the aqueous fraction was extracted with ethyl acetate (3×150 ml). The organic layers were combined, washed with a saturated sodium chloride solution, dried over potassium carbonate, filtered, and the solvents were removed in vacuo to yield 3.6 grams of a brown/pink solid.

The desired intermediate was further purified by chromatography using a hexanes/ethyl acetate (3:1) solution as the eluent to yield a light pink solid. mp 162–164° C.

The intermediate prepared above (3.40 grams, 9.6 mmol) was dissolved in chloroform (90 ml). This solution was stirred at room temperature as phosphorous oxychloride in chloroform (40 ml) was added dropwise. The reaction mixture was refluxed overnight.

The reaction mixture was partitioned with 1N sodium hydroxide and the organic layer removed. The aqueous fraction was further extracted with methylene chloride (3×150 ml). The organic layers were combined, washed with a saturated sodium chloride solution, dried over potassium carbonate, filtered, and the solvents were removed in vacuo.

The reaction product was further purified by chromatography to yield 2.64 grams (82.1%) of a light pink solid. MS 335, 337, mp 183–185° C.

Analysis for $C_{20}H_{15}ClN_2O$: Theory: C, 71.75; H, 4.52; N, 8.37. Found: C, 71.67; H, 4.77; N, 8.59.

EXAMPLE 18
Synthesis of 1-phenyl-2-(4-methylphenyl)benzimidazole

A solution of N-phenyl-o-phenylenediamine (1.84 g, 10 mmol) in diethyl ether (85 ml) was stirred at room temperature as p-toluoyl chloride (1.60 g, 10 mmol) in diethyl ether (35 ml) was added dropwise. The reaction mixture was stirred overnight at room temperature.

The reaction mire was alkalinized with 1N sodium hydroxide. The organic layer was removed and the aqueous fraction was extracted with ethyl acetate (3×150 ml). The organic layers were combined, washed with a saturated sodium chloride solution, dried over potassium carbonate, filtered, and the solvents were removed in vacuo to yield 3.18 grams of a red/brown solid.

The intermediate was further purified by chromatography using a hexanes/ethyl acetate (9:1) solution as the eluent to yield a yellow solid. mp 143–145° C.

The intermediate prepared above (2.63 g, 8.6 mmol) was dissolved in chloroform (85 ml). This solution was stirred at room temperature as phosphorous oxychloride (1.35 g, 8.6 mmol) in chloroform (30 ml) was added dropwise. The reaction mixture was refluxed overnight.

The reaction mixture was partitioned with 1N sodium hydroxide and the organic layer removed. The aqueous layer was extracted with methylene chloride (3×150 ml). The organic fractions were combined, washed with a saturated sodium chloride solution, dried over potassium carbonate, filtered and the solvents were removed in vacuo to yield a red/brown oil which solidified upon standing.

The reaction product was further purified by chromatography using a hexanes/ethyl acetate (4:1) solution as the eluent. The fractions were combined, the solvents removed in vacuo and the resulting oil was triturated with diethyl ether. The title product was recrystallized from diethyl ether/hexanes to yield 1.54 grams (63%). MS 285(M$^+$)

Analysis for $C_{20}H_{16}N_2$: Theory: C, 84.48; H, 5.67; N, 9.85. Found: C, 85.60; H, 5.94; N, 10.45.

EXAMPLE 19
Synthesis of 1-phenyl-2-(3-methylphenyl)benzimidazole

A solution of N-phenyl-o-phenylenediamine (1.84 g, 10 mmol) in diethyl ether (90 ml) was stirred at room temperature as m-toluoyl chloride (1.55, 10 mmol) in diethyl ether (30 ml) was added dropwise. The reaction mixture was stirred at room temperature overnight.

The reaction mixture was then alkalinized with 1N sodium hydroxide. The organic layer was removed and the aqueous fraction was extracted with ethyl acetate (3×150 ml). The organic fractions were combined, washed with a saturated sodium chloride solution, dried over potassium carbonate, filtered, and the solvents were removed in vacuo to yield 3.12 grams of a gray/brown solid.

The intermediate was further purified by chromatography. mp 129–130° C.

The intermediate prepared above (2.5 g, 8.3 mmol) in chloroform (95 ml) was stirred at room temperature as phosphorous oxychloride (1.30 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent. The product was recrystallized from hexanes to yield 0.97 grams (41.1%) of a white solid.

MS 285(M$^+$), mp 69–71° C.

Analysis for $C_{20}H_{16}N_2$: Theory: C, 84.48; H, 5.67; N, 9.85. Found: C, 84.48; H, 5.72; N, 9.80.

EXAMPLE 20
Synthesis of 1-phenyl-2-(4-cyanophenyl)benzimidazole

A solution of N-phenyl-o-phenylenediamine (1.84 g, 10 mmol) in diethyl ether (100 ml) was stirred at room temperature as 4-cyanobenzoyl chloride (1.66 g, 10 mmol) in diethyl ether (40 ml) was added dropwise. The reaction mixture was stirred overnight at room temperature.

The reaction mixture was partitioned with 1N sodium hydroxide. The organic fraction was removed and the aqueous layer was extracted with ethyl acetate (3×150 ml). The combined organic layers were washed with a saturated sodium chloride solution, dried over potassium carbonate, filtered and the solvents were removed in vacuo to yield 3.31 grams of a red/black oily gum.

This oily gum (2.8 g, 8.9 mmol) was dissolved in chloroform (90 ml). This solution was stirred as phosphorous oxychloride (1.40 g, 9.0 mmol) in chloroform (35 ml) was added dropwise. This reaction mixture was refluxed overnight.

The reaction mixture was alkalinized with 1N sodium hydroxide. The organic layer was removed and the aqueous fraction was extracted with methylene chloride (3×150 ml). The organic layers were combined, washed with a saturated sodium chloride solution, dried over potassium carbonate, filtered, and the solvents were removed in vacuo to yield a red/brown oil.

The reaction product was further purified by chromatography using a hexanes/ethyl acetate solution as eluent. The title product then was recrystallized from ethyl acetate to yield a white solid MS 296(M$^+$), mp 182–184° C.

Analysis for $C_{20}H_{13}N_3$: Theory: C, 81.34; H, 4.44; N, 14.23. Found: C, 81.55; H, 4.50; N, 14.47.

EXAMPLE 21
Synthesis of 1-phenyl-2-cyclohexylbenzimidazole

A solution of N-phenyl-o-phenylenediamine (1.84 g, 10 mmol) in diethyl ether (85 ml) was stirred at room temperature as cyclohexanecarbonyl chloride (1.46 grams, 10 mmol) in diethyl ether (3 ml) was added dropwise. The reaction mixture was stirred at room temperature overnight.

The reaction mixture was alkalinized with 1N sodium hydroxide. The organic fraction was removed and the aqueous phase was extracted with ethyl acetate (3×150 ml). The organic fractions were combined, washed with saturated sodium chloride solution, dried over potassium carbonate, filtered, and the solvents were removed in vacuo to yield 2.81 grams of a brown solid. The reaction product was further purified by chromatography to yield N-phenyl-N'-cyclohexylcarbonylphenylenediamine as a yellow solid.

The intermediate prepared above (2.0 g, 7 mmol) was dissolved in chloroform (80 ml). This solution was stirred at room temperature as phosphorous oxychloride (1.05 g, 7 mmol) in chloroform (30 ml) was added dropwise. The reaction mixture was refluxed overnight.

The reaction mixture was alkalinized with 1N sodium hydroxide. The organic layer was removed and the aqueous layer was extracted with methylene chloride (3×150 ml). The organic fractions were combined, washed with a saturated sodium chloride solution, dried over potassium carbonate, filtered, and the solvents were removed in vacuo to yield 2.81 grams of a black/red oil which solidified upon standing.

The reaction product was further purified by partitioning between 1N hydrochloric acid and an ethyl acetate/hexanes (1:1) solution. The aqueous layer was alkalinized to pH 10 using 1N sodium hydroxide. The aqueous fraction was then extracted with ethyl acetate (4×250 ml). The organic layers were combined, washed with a saturated sodium chloride solution, dried over potassium carbonate, filtered and the solvents were removed in vacuo to yield 1.47 grams (76%) of a light yellow solid MS 277($M^+$), mp 99–101° C.

Analysis for $C_{19}H_{20}N_2$: Theory: C, 82.57; H, 7.29; N, 10.14. Found: C, 82.33; H, 7.45; N, 10.21.

EXAMPLE 22
Synthesis of 1-phenyl-2-(2-chlorophenyl)benzimidazole

A solution of N-phenyl-o-phenylenediamine (1.84 g, 10 mmol) in diethyl ether (85 ml) was stirred at room temperature as 2-chlorobenzoyl chloride (1.76 g, 10 mmol) in diethyl ether (35 ml) was added dropwise. The reaction mixture was stirred overnight at room temperature.

The reaction mixture was alkalinized with 1N sodium hydroxide and the organic layer removed. The aqueous phase was extracted with ethyl acetate (3×100 ml). The organic fractions were combined, washed with a saturated sodium chloride solution, dried over potassium carbonate, filtered, and the solvents were removed in vacuo to yield 3.2 grams (>99%) of a gray/brown solid.

The crude product prepared supra (2.7 g, 8.4 mmol) was dissolved in chloroform (95 ml). This solution was stirred at room temperature as phosphorous oxychloride (1.3 g, 8.5 mmol) in chloroform (30 ml) was added dropwise. The reaction mixture was refluxed overnight and then partitioned with 1N sodium hydroxide.

The organic layer was removed and the aqueous phase was extracted with methylene chloride (3×150 ml). The combined organic layers were washed with a saturated sodium chloride solution, dried over potassium carbonate, filtered, and the solvents were removed in vacuo.

The crude product was further purified by chromatography using a hexanes/ethyl acetate (9:1) solution as the eluent. The recovered product was triturated in hexanes and filtered to yield 1.31 grams (51.2%) of a light yellow solid. MS 305, 307, mp 146–148° C.

Analysis for $C_{19}H_{13}ClN_2$: Theory: C, 74.88; H, 4.30; N, 9.19. Found: C, 75.16; H, 4.31; N, 9.21.

EXAMPLE 23
Synthesis of 1-phenyl-2-(2-methylphenyl)benzimidazole

A solution of N-phenyl-o-phenylenediamine (1.84 g, 10 mmol) in diethyl ether (90 ml) was stirred at room temperature as o-toluoyl chloride (1.55 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (3:1) solution as the eluent. Trituration with hexanes and subsequent filtration yielded a white solid. mp 118–120° C.

The intermediate prepared above (2.52 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1 to 4:1) solution as the eluent to yield a pale yellow oil. The product was triturated with hexanes to yield a light yellow solid. MS 285($M^+$), mp 99–101° C.

Analysis for $C_{20}H_{16}N_2$: Theory: C, 84.48; H, 5.67; N, 9.85. Found: C, 84.48; H, 5.72; N, 9.80.

EXAMPLE 24
Synthesis of 1-phenyl-2-(2-methoxyphenyl)benzimidazole

A solution of N-phenyl-o-phenylenediamine (1.84 g, 10 mmol) in diethyl ether (90 ml) was stirred at room temperature as 2-methoxybenzoyl chloride (1.55 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (9:1) solution as eluent. The reaction product was recrystallized from hexanes. mp 178–180° C.

The intermediate prepared above (2.65 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent to yield 1.64 grams (65.7%) of the title product as a white solid. MS 301($M^+$), mp 159–160° C.

Analysis for $C_{20}H_{16}N_2O$: Theory: C, 79.98; H, 5.37; N, 9.33. Found: C, 80.01; H, 5.36; N, 9.40.

EXAMPLE 25
Synthesis of 1-phenyl-2-(3-cyanophenyl)benzimidazole

A solution of N-phenyl-o-phenylenediamine (1.84 g, 10 mmol) in diethyl ether (90 ml) was stirred at room temperature as 3-cyanobenzoyl chloride (1.66 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (4:1) solution as the eluent. The product was recrystallized from hexanes to yield a white solid mp 141–143° C.

The intermediate prepared above (2.63 g, 8.3 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1 to 4:1) solution as eluent. The title product was recrystallized from hexanes and ethyl acetate. MS 296($M^+$), mp 153–154° C.

Analysis for $C_{20}H_{13}N_3$: Theory: C, 81.34; H, 4.44; N, 14.23. Found. C, 81.60; H. 4.45; N, 14.38.

EXAMPLE 26

Synthesis of 1-dimethylaminoethyl-2-phenylbenzimidazole dihydrochloride

A solution of 2-phenylbenzimidazole (0.97 g, 5 mmol) in N,N-dimethylformamide (anhydrous, 20 ml) was stirred at room temperature under nitrogen atmosphere. Two equivalents of sodium hydride in 60% dispersion (0.40 g, 10 mmol) was quickly added and the reaction mixture was allowed to stir under nitrogen. N,N-Dimethylaminoethyl bromide hydrobromide (1.16 g, 5 mmol) in anhydrous N,N-dimethylformamide (12 ml) was added dropwise by syringe to the stirring mixture. The reaction mixture was stirred overnight at room temperature.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield 1.11 grams of a cloudy oil.

The crude product was stirred with 2N hydrochloric acid in ethanol. The solvents were removed in vacuo to yield 1.16 (66.8%) grams of the title product as a white solid. MS 309, mp 228–231° C.

Analysis for $C_{17}H_{19}N_3$ .2 HCl: Theory: C, 60.36; H, 6.26; N, 12.42. Found: C, 60.09; H, 6.22; N, 12.18.

EXAMPLE 27

Synthesis of 1-phenyl-2-(3,4-dichlorophenyl)benzimidazole

A solution of N-phenyl-o-phenylenediamine (1.84 g, 10 mmol) in diethyl ether (90 ml) was stirred at room temperature as 3,4-dichlorobenzoyl chloride (2.10 g, 10 mmol) in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (4:1) solution as the eluent. The product was recrystallized from hexanes to yield a white solid. mp 146–147° C.

The intermediate prepared above (3.00 g, 8.4 mmol) in chloroform (95 ml) was stirred at room temperature as phosphorous oxychloride (133 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (4:1) solution as eluent. The title product was recrystallized from hexanes and ethyl acetate as a white solid. MS 339, 341, mp 144–146° C.

Analysis for $C_{19}H_{12}Cl_2N_2$: Theory: C, 67.27; H, 3.57; N, 8.26. Found: C, 67.53; H, 3.61; N, 8.13.

EXAMPLE 28

Synthesis of 1-(piperidin-1-ylethyl)-2-phenylbenzimidazole dihydrochloride

A solution of 2-phenylbenzimidazole (0.97 g, 5 mmol) in N,N-dimethylformamide (anhydrous, 20 ml) was stirred at room temperature under nitrogen atmosphere. Two equivalents of sodium hydride in 60% dispersion (0.40 g, 10 mmol) was quickly added and the reaction mixture was allowed to stir under nitrogen. N-(2-chloroethyl)piperidinyl (10 mmol) in anhydrous N,N-dimethylformamide (12 ml) was added dropwise by syringe to the stirring mixture. The reaction mixture was stirred overnight at room temperature.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield 1.11 grams of a cloudy oil.

This was then stirred in 2N hydrochloric acid in ethanol. The solvents were removed in vacuo, yielding the crude product, which was recrystallized twice from an ethyl acetate/ethanol solution. The solvents were removed in vacuo to yield 0.95 grams (50.2%) of the title product as a white solid. MS 306

Analysis for $C_{20}H_{23}N_3$.2 HCl: Theory: C, 63.49; H, 6.66; N, 11.11. Found: C, 63.33; H, 6.64; N, 10.92.

EXAMPLE 29

Synthesis of 1-phenyl-2-(4-hydroxyphenyl)benzimidazole

A solution of 1-phenyl-2-(4-methoxyphenyl) benzimidazole(0.60 g, 2.0 mmol) in hydrobromic acid (6 ml) and acetic acid (6 ml) was refluxed for 40 hours. The reaction mixture was extracted with diethyl ether (5×150 ml) at a pH of 3–5. The organic solvents were discarded. The aqueous phase was alkalinized to pH 8–9 and extracted with ethyl acetate (5×150 ml). The organic fractions were combined and dried over potassium carbonate, then filtered and the solvents were removed in vacuo to yield a white solid. The solid was triturated in diethyl ether and filtered to yield 0.25 grams of the desired product.

Analysis for $C_{19}H_{14}N_2O$ . 0.5 $H_2O$: Theory: C, 77.27; H, 5.12; N, 9.48. Found: C, 77.56; H, 4.96; N, 9.39.

EXAMPLE 30

Synthesis of 1-phenyl-2-(3-nitro-4-chlorophenyl)-benzimidazole

A solution of N-phenyl-o-phenylenediamine (1.84 g, 10 mmol) and 4-chloro-3-nitro-benzoic acid (2.07 g, 10 mmol) in anhydrous tetrahydrofuran was stirred at room temperature as N-ethoxycarbonyl-2 -ethoxy-1,2-dihydroquinoline (3.71 g, 15 mmol) in tetrahydrofuran was added dropwise. The reaction was stirred at room temperature for about 72 hours.

The reaction mixture was alkalinized with 1N sodium hydroxide. The aqueous layer was extracted with ethyl acetate (4×100 ml). The organic fractions were combined, dried over potassium carbonate, filtered, and the solvents removed in vacuo to yield the crude product.

The reaction product was further purified by chromatography using a hexanes/ethyl acetate (4:1) solution as eluent.

The intermediate prepared above (3.00 g, 8.4 mmol) in chloroform (95 ml) was stirred at room temperature as phosphorous oxychloride (1.33 g, 8.4 mmol) in chloroform (30 ml) was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (9:1) solution as eluent. The title product was recrystallized from fractions with ethyl acetate as a white solid. MS 349, 351, mp 179–182° C.

Analysis for $C_{19}H_{12}ClN_3O_2$: Theory: C, 65.24; H, 3.46; N, 12.01. Found: C, 65.50; H, 3.51; N, 12.06.

EXAMPLE 31

Synthesis of 1-[2-(morpholin-4-yl)ethyl]-2-phenylbenzimidazole dihydrochloride

A solution of 2-phenylbenzimidazole (0.97 g, 5 mmol) in N,N-dimethylformamide (anhydrous, 20 ml) was stirred at 60° C. under nitrogen atmosphere. Two equivalents of sodium hydride in 60% dispersion (0.40 g, 10 mmol) was quickly added and the reaction mixture was allowed to stir under nitrogen. N-(2-chloroethyl)morpholine (0.93 g, 5 mmol) in anhydrous N,N-dimethylformamide (12 ml) was added dropwise by syringe to the stirring mixture. The reaction mixture was stirred overnight at 60° C.

The reaction mixture was partitioned between acetic acid and ethyl acetate. The organic layer was discarded and the aqueous phase was extracted with diethyl ether (5×75 ml). All organic fractions were discarded.

The aqueous phase was alkalinized with 2N sodium hydroxide. This solution was then extracted with diethyl ether (4×100 ml). The organic fractions were combined, washed with a saturated sodium chloride solution, dried over potassium carbonate, filtered, and the solvents were removed in vacuo to yield a cloudy oil.

The crude product was mixed with a 2N hydrochloric acid/ethanol (1:1) solution. The solvents were removed in vacuo to yield 1.52 grams (40%) of a white solid. MS 308.

Analysis for $C_{19}H_{21}N_3O \cdot 2\ HCl \cdot EtOH$: Theory: C, 59.16; H, 6.86; N, 9.85. Found: C, 59.20; H, 6.85; N, 9.89.

EXAMPLE 32

Synthesis of 1-phenyl-2-propylbenzimidazole

A solution of N-phenyl-o-phenylenediamine (1.84 g, 10 mmol) in tetrahydrofuran (90 ml) was stirred at room temperature under a nitrogen atmosphere as butanoyl chloride (1.28 g, 12 mmol) in tetrahydrofuran (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo.

The reaction product was further purified by chromatography using a hexanes/ethyl acetate (3:1) solution as the eluent. The product was recrystallized from hexanes to yield a white solid.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (3:1) solution as eluent. The title product was recrystallized from hexanes and ethyl acetate as a white solid, yielding 1.55 grams (66%). MS 237, mp 53–55° C.

Analysis for $C_{16}H_{16}N_2$: Theory: C, 81.32; H, 6.82; N, 11.85. Found: C, 81.06; H, 6.69; N, 12.02.

EXAMPLE 33

Synthesis of 1-phenyl-2-(thien-2-yl)benzimidazole

A solution of N-phenyl-o-phenylenediamine (1.84 g, 10 mmol) in diethyl ether (90 ml) was stirred at room temperature under a nitrogen atmosphere as an equimolar amount of 2-chlorocarbonylthiophene in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether. Recrystallization from ethyl acetate yielded a white solid which was homogeneous on thin layer chromatography. mp 150–152° C.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo.

The reaction product was further purified by chromatography using a hexanes/ethyl acetate (3:1) solution as eluent. The title product was recrystallized from hexanes and ethyl acetate as clear crystals. The solvent was removed in vacuo, yielding 1.70 grams (64%). MS 277, mp 118–120° C.

Analysis for $C_{17}H_{12}N_2S$: Theory: C, 73.62; H, 4.72; N, 10.10. Found: C, 73.84; H, 4.48; N, 10.30.

EXAMPLE 34

Synthesis of 1-phenyl-2-(3-hydroxyphenyl)benzimidazole

A solution of 1-phenyl-2-(3-methoxyphenyl)benzimidazole (0.20 g, 0.67 mmol) and hydrobromic acid (4 ml) and acetic acid (4 ml) was refluxed for 48 hours. The reaction mixture was cooled and extracted with diethyl ether (5×150 ml) at pH 3–5. The organic fractions were discarded. The aqueous phase was alkalinized to pH 8–9 and extracted with ethyl acetate (5×150 ml). The organic layers were combined, washed with a saturated sodium chloride solution, dried over magnesium sulfate, filtered, and the solvents were removed in vacuo to yield a white solid. The solid was triturated with an ethyl acetate/diethyl ether mixture.

The reaction product was further purified by chromatography to yield 0.17 grams (88.6%) of a white solid. MS 287(M$^+$), mp 245–247°C.

Analysis for $C_{19}H_{14}N_2O \cdot 2\ H_2O$: Theory: C, 78.71; H, 5.01; N, 9.66. Found: C, 78.79; H, 5.16; N, 9.70.

EXAMPLE 35
Synthesis of 1-phenyl-2-pentylbenzimidazole hydrochloride

A solution of N-phenyl-o-phenylenediamine (1.84 g, 10 mmol) in diethyl ether (90 ml) was stirred at room temperature as an equimolar amount of hexanoyl chloride in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether. Recrystallization from ethyl acetate yielded a white solid which was homogeneous on thin layer chromatography.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo to yield a red/brown oil.

The reaction product was further purified by chromatography using a hexanes/ethyl acetate (3:1) solution as eluent to yield 1.82 grams (69.2%) as a red oil. The red oil was stirred in a 2N hydrochloric acid/ethanol (1:1) solution for ten minutes. The ethanol was removed in vacuo to yield 2.1 grams of a brown/green solid. The title product was recrystallized from an ethyl acetate/ethanol (1:1) solution. The solvent was removed in vacuo, yielding 1.56 grams (51.9%) of the title product as a white solid. MS 265(M$^+$), mp 202–205° C.

Analysis for $C_{18}H_{20}N_2 \cdot HCl$: Theory: C, 71.87; H, 7.04; N, 9.31. Found: C, 72.02; H, 7.23; N, 9.05.

EXAMPLE 36
Synthesis of 1-phenyl-2-(2-trifluoromethylphenyl)-benzimidazole

A solution of N-phenyl-o-phenylenediamine (1.84 g, 10 mmol) in diethyl ether (90 ml) was stirred at room temperature as an equimolar amount of 2-trifluoromethylbenzoyl chloride in diethyl ether (35 ml) was added dropwise. The reaction mixture was stirred overnight at room temperature.

The reaction mixture was alkalinized with 1N sodium hydroxide and the organic layer was removed. The aqueous fraction was extracted with ethyl acetate (3×100 ml). The organic fractions were combined, washed with a saturated sodium chloride solution, dried over potassium carbonate, filtered, and the solvents were removed in vacuo to yield a red/brown oil.

The reaction product was further purified by trituration in diethyl ether to yield a white solid which was homogeneous on thin layer chromatography. mp 161–162° C.

The intermediate prepared above in chloroform was stirred at room temperature as an equimolar amount of phosphorous oxychloride in chloroform was added dropwise. The reaction mixture was refluxed overnight.

The reaction mixture was alkalinized with 1N sodium hydroxide and the organic layer was removed. The aqueous layer was extracted with methylene chloride (3×150 ml). The organic layers were combined, washed with a saturated sodium chloride solution, dried over potassium carbonate, filtered, and the solvents were removed in vacuo to yield a red/brown mixture of oil and solid.

The reaction product was further purified by chromatography using a hexanes/ethyl acetate (3:1) solution as eluent followed by trituration in diethyl ether to yield 1.07 grams (37.2%). Recrystallization from hexanes yielded white crystals, homogeneous on thin layer chromatography. MS 338, mp 142–144° C.

Analysis for $C_{20}H_{13}F_3N_2$: Theory: C, 71.00; H, 3.87; N, 8.28. Found: C, 70.70; H, 3.97; N, 8.12.

EXAMPLE 37
Synthesis of 1-benzyl-2-(3,4,5-trimethoxyphenyl)-benzimidazole

A solution of o-phenylenediamine dihydrochloride (3.62 g, 20 mmol), 3,4,5-trimethoxybenzaldehyde (3.92 g, 20 mmol) and triethylamine (2.02 g, 20 moles) in nitrobenzene (100 mls) was heated at 150° C. for 32 hours. The majority of the nitrobenzene was distilled off by vacuum distillation (60° C. pot temperature, 0.1 mm Hg). The crude product was partitioned between 1N sodium hydroxide and ethyl acetate. The ethyl acetate fraction was removed and the aqueous phase was extracted with ethyl acetate (3×100 ml).

The organic fractions were combined, washed with brine, dried over sodium sulfate, filtered, and the solvents were removed in vacuo to yield a red brown oil which was purified by column chromatography using a hexanes/ethyl acetate (1:1) solution as the eluting solvent to yield the intermediate 2-(3,4,5-trimethoxyphenyl)benzimidazole. NMR The intermediate prepared above (0.91 g, 3.2 mmol) and sodium hydride (0.26 g, 6.4 mmol) in N,N-dimethylformamide (25 ml) were stirred at room temperature as benzyl bromide (0.60 g, 6.4 mmol) was added dropwise. The resulting mixture was stirred at room temperature for 30 minutes and then heated to 120° C. where it was maintained for seven days. Additional sodium hydride and benzymbromide were added as needed force the reaction forward.

The crude product was partitioned between water and ethyl acetate, followed by an acid/base workup in a separatory funnel. The organic layers were washed with brine, dried over potassium carbonate, filtered, and the solvents were removed in vacuo. MS 375(M$^+$)

Analysis for $C_{23}H_{22}N_2O_3$: Theory: C, 73.78; H, 5.92; N, 7.48. Found: C, 73.99; H, 5.95; N, 7.19.

EXAMPLES 38 AND 39
Synthesis of 1-phenylmethyl-2-(3,4,5-trimethoxyphenyl)-5-methoxybenzimidazole (Example 38) and 1-phenylmethyl-2-(3,4,5-trimethoxyphenyl)-6-methoxybenzimidazole (Example 39)

This synthesis was performed essentially as described in Example 37 except for the substitution of 4-methoxy-o-phenylenediamine in place of the o-phenylenediamine employed there. This resulted in a mixture of the regioisomers of the title products which could be separated using common techniques.

EXAMPLE 38: MS 404, Analysis for $C_{24}H_{24}N_2O_4$: Theory: C, 71.27; H, 5.98; N, 6.92. Found: C, 71.07; H, 6.16; N, 6.89.

EXAMPLE 39: MS 404, Analysis for $C_{24}H_{24}N_2O_4$: Theory: C, 71.27; H, 5.98; N, 6.93. Found: C, 71.24; H, 6.11; N, 6.97.

EXAMPLE 40

Synthesis of 1-(3-chlorobenzyl)-2-(3,4,5-trimethoxyphenyl)-benzimidazole

An amount of 2-(3,4,5-trimethoxyphenyl)-benzimidazole (1.05 g, 3.69 mmol), prepared as described in Example 37, supra, was added to a three-neck flask with a stir bar. The contents of the flask were placed under nitrogen atmosphere and 50 ml of N,N-dimethylformamide was added by syringe. This mixture was then allowed to stir. Sodium hydride (60%, 0.41 g, 4.10 mmol) was then added to the reaction mixture and the resulting mixture was stirred for about 30 minutes.

The resulting grayish mixture was then placed into an oil bath and 3-chlorobenzyl bromide (0.60 ml, 4.10 mmol) was added. The temperature of the solution was then raised to 60° C. and the solution was allowed to stir overnight.

The solution was then removed from the oil bath and allowed to cool to room temperature. Ethyl acetate (150 ml) was then added to the reaction mixture. This organic solution was extracted with water (3×150 ml), followed by 25 ml of diethyl ether. The organic phase was then washed with a saturated sodium chloride solution.

The organic solution was reduced in vacuo to yield a yellow oil. To this oil ethanol (50 ml) and hexanes (20 ml) were added. The yellow solution was cooled and allowed to crystallize. The crystals were recovered by filtration and then washed with 20 ml of hexanes. The liquors were reduced in vacuo and allowed to crystallize to yield a total of 1.05 grams of the title product. MS 409, 411, mp 83° C.

Analysis for $C_{23}H_{21}ClN_2O_3$: Theory: C, 67.56; H, 5.18; N, 6.85. Found: C, 67.82; H, 5.21; N, 6.64.

EXAMPLE 41

Synthesis of 1-(2-chlorobenzyl)-2-(3,4,5-trimethoxyphenyl)-benzimidazole

The title product was prepared essentially as described in Example 40, supra, except that 2-chlorobenzyl bromide (0.50 ml, 4.19 mmol) was employed instead of the 3-chlorobenzyl bromide, to yield 1.13 g (80%). MS 409, 411, mp 173.5° C.

Analysis for $C_{23}H_{21}ClN_2O_3$: Theory: C, 67.56; H, 5.18; N, 6.85. Found: C, 67.33; H, 5.21; N, 6.60.

EXAMPLE 42

Synthesis of 1-(4-chlorobenzyl)-2-(3,4,5-trimethoxyphenyl)-benzimidazole

The title compound was prepared essentially as described in Example 40, supra, except that 4-chlorobenzyl bromide (0.75 g, 4.03 mmol) was employed instead of the 3-chlorobenzyl bromide. MS 409, 411, mp 169° C.

Analysis for $C_{23}H_{21}ClN_2O_3$: Theory: C, 67.56; H, 5.18; N, 6.85. Found: C, 68.07; H, 5.34; N, 6.46.

EXAMPLE 43

Synthesis of 1-(2-methylbenzyl)-2-(3,4,5-trimethoxyphenyl)-benzimidazole

The title compound was prepared essentially as described in Example 40, supra, except that α-bromo-o-xylene (0.55 g, 4.10 mmol) was employed instead of the 3-chlorobenzyl bromide. MS 389, mp 140.5° C.

Analysis for $C_{24}H_{24}N_2O_3$: Theory: C, 74.21; H, 6.23; N, 7.21. Found: C, 73.92; H, 6.25; N, 7.05.

EXAMPLE 44

Synthesis of 1-(3-methylbenzyl)-2-(3,4,5-trimethoxyphenyl)-benzimidazole

The title compound was prepared essentially as described in Example 40, supra, except that α-bromo-m-xylene (0.55 g, 4.10 mmol) was employed instead of the 3-chlorobenzyl bromide. MS 389, mp 78° C.

Analysis for $C_{24}H_{24}N_2O_3$: Theory: C, 74.21; H, 6.23; N, 7.21. Found: C, 73.96; H, 6.34; N, 7.01.

EXAMPLE 45

Synthesis of 1-(3-methoxybenzyl)-2-(3,4,5-trimethoxyphenyl)-benzimidazole

The title compound was prepared essentially as described in Example 40, supra, except that 3-methoxybenzyl chloride (0.60 ml, 4.13 mmol) was employed instead of the 3-chlorobenzyl bromide. MS 405, mp 127° C.

Analysis for $C_{24}H_{24}N_2O_4$: Theory: C, 71.27; H, 5.98; N, 6.93. Found: C, 71.21; H, 6.04; N, 6.98.

EXAMPLE 46

Synthesis of 1-(4methoxybenzyl)-2-(3,4,5-trimethoxyphenyl)-benzimidazole

The title compound was prepared essentially as described in Example 40, supra, except that 4-methoxybenzyl chloride (0.60 ml, 4.13 mmol) was employed instead of the 3-chlorobenzyl bromide. MS 405, mp 110.5° C.

Analysis for $C_{24}H_{24}N_2O_4$: Theory: C, 71.27; H, 5.98; N, 6.93. Found: C, 71.01; H, 6.01; N, 7.08.

EXAMPLE 47

Synthesis of 1-(2-methoxybenzyl)-2-(3,4,5-trimethoxyphenyl)-benzimidazole

The title compound was prepared essentially as described in Example 40, supra, except that 2-methoxybenzyl chloride (50% 1.26 ml, 4.13 mmol) was employed instead of the 3-chlorobenzyl bromide. This reaction was performed at room temperature and allowed to stir for about six hours. MS 405, mp 136° C.

Analysis for $C_{24}H_{24}N_2O_4$: Theory: C, 71.27; H, 5.98; N, 6.93. Found: C, 71.47; H, 6.13; N, 6.92.

EXAMPLE 48

Synthesis of 1-(2-fluorobenzyl)-2-(3,4,5-trimethoxyphenyl)-benzimidazole

The title compound was prepared essentially as described in Example 40, supra, except that 2-fluorobenzyl bromide (0.48 ml, 4.33 mmol) was employed instead of the 3-chlorobenzyl bromide. MS 392, mp 153.5° C.

Analysis for $C_{23}H_{21}FN_2O_3$: Theory: C, 70.40; H, 5.39; N, 7.14. Found: C, 70.15; H, 5.37; N, 7.14.

EXAMPLE 49

Synthesis of 1-(2-trifluoromethylbenzyl)-2-(3,4,5-trimethoxyphenyl)-benzimidazole The title compound was prepared essentially as described in Example 40, supra, except that 2-trifluoromethylbenzyl bromide (0.48 ml, 4.33 mmol) was employed instead of the 3-chlorobenzyl bromide. MS 442, mp 144° C.

Analysis for $C_{24}H_{21}F_3N_2O_3$: Theory: C, 65.15; H, 4.78; N, 6.33. Found: C, 65.18; H, 4.75; N, 6.28.

EXAMPLE 50

Synthesis of 1-(2-iodobenzyl)-2-(3,4,5-trimethoxyphenyl)-benzimidazole

The title compound was prepared essentially as described in Example 40, supra, except that 2-iodobenzyl bromide (1.0 ml, 4.33 mmol) was employed instead of the 3-chlorobenzyl bromide. MS 500, mp 179° C.

Analysis for $C_{23}H_{21}IN_2O_3$: Theory: C, 55.21; H, 4.23; N, 5.60. Found: C, 55.26; H, 4.27; N, 5.71.

EXAMPLE 51
Synthesis of 1-(2-bromobenzyl)-2-(3,4,5-trimethoxyphenyl)-benzimidazole The title compound was prepared essentially as described in Example 40, supra, except that 2-bromobenzyl bromide (1.0 ml, 4.33 mmol) was employed instead of the 3-chlorobenzyl bromide. MS 452, 454, mp 152° C.

Analysis for $C_{23}H_{21}BrN_2O_3$: Theory: C, 60.94; H, 4.67; N, 6.18. Found: C, 61.18; H, 4.62; N, 6.09.

EXAMPLE 52
Synthesis of 1-(2,6-dichlorobenzyl)-2-(3,4,5-trimethoxyphenyl)-benzimidazole The title compound was prepared essentially as described in Example 40, supra, except that 2,6-dichlorobenzyl bromide (0.81 g, 4.10 mmol) was employed instead of the 3-chlorobenzyl bromide. mp 157° C. MS 443, 445, NMR, IR.

Analysis for $C_{23}H_{20}Cl_2N_2O_3$: Theory: C, 62.31; H, 4.55; N, 6.32. Found: C, 62.84; H, 4.57; N, 6.31.

EXAMPLE 53
Synthesis of 1-(3,4-dichlorobenzyl)-2-(3,4,5-trimethoxyphenyl)-benzimidazole The title compound was prepared essentially as described in Example 40, supra, except that 3,4-dichlorobenzyl bromide (0.90 g, 4.45 mmol) was employed instead of the 3-chlorobenzyl bromide. mp 145° C., MS 443, 445, NMR, IR.

Analysis for $C_{23}H_{20}Cl_2N_2O_3$: Theory: C, 62.31; H, 4.55; N, 6.32. Found: C, 62.35; H, 4.65; N, 6.17.

EXAMPLE 54
Synthesis of 1-(2,4-dichlorobenzyl)-2-(3,4,5-trimethoxyphenyl)-benzimidazole The title compound was prepared essentially as described in Example 40, supra, except that 2,4-dichlorobenzyl bromide (0.45 g, 2.23 mmol) was employed instead of the 3-chlorobenzyl bromide. mp 186° C. MS 443, 445, NMR, IR.

Analysis for $C_{23}H_{20}Cl_2N_2O_3$: Theory: C, 62.31; H, 4.55; N, 6.32. Found: C, 62.22; H, 4.65; N, 6.34.

EXAMPLE 55
Synthesis of 1-(4-methylbenzyl)-2-(3,4,5-trimethoxyphenyl)-benzimidazole The title compound was prepared essentially as described in Example 40, supra, except that 4-methylbenzyl bromide (0.45 g, 2.23 mmol) was employed instead of the 3-chlorobenzyl bromide. MS 389, mp 84.5° C.

Analysis for $C_{24}H_{24}N_2O_3$: Theory: C, 74.21; H, 6.23; N, 7.21. Found: C, 73.91; H, 6.23; N, 6.98.

EXAMPLE 56
Synthesis of 1-(2-chlorobenzyl)-2-(3-methylphenyl)-benzimidazole

The intermediate 2-(3-methylphenyl)-benzimidazole was prepared by first mixing reacting 1-amino-2-nitrobenzene (8.50 g, 61.54 mmol) with toluene (180 ml) and heating to 100° C. To this mixture was then added 20 ml of N,N-diethylaniline and the reaction vessel was placed under a nitrogen atmosphere. To this solution was then added 3-methylbenzoyl chloride (24 ml, 132 mmol) and this mixture was then stirred overnight.

After stirring, the reaction mixture was neutralized by the addition of 300 ml of 1N hydrochloric acid and 300 ml of ethyl acetate. This was then stirred for about 30 minutes. The organic phase was then removed and washed with water, followed by drying over magnesium sulfate and reduction in vacuo, yielding yellow crystals of the intermediate 1-[(3-methylphenyl)carbonylamino]-2-nitrobenzene. The nitro group of the above intermediate was then reduced by catalytic hydrogenation employing a palladium on activated carbon catalyst resulting in the substituted 1,2-phenylenediamine.

The substituted 1,2-phenylenediamine (1.01 g, 4.46 mmol) was then cyclized using phosphorous oxychloride (1.01 g, 6.6 mmol) as described supra to produce 2-(3-methylphenyl)benzimidazole.

The title compound was then produced by reacting the 2-(3-methylphenyl)benzimidazole (0.75 g, 3.60 mmol) with 2-chlorobenzyl chloride (0.50 ml, 4.19 mmol) essentially as described in Example 40, supra. MS 332, 334, mp 117° C.

Analysis for $C_{21}H_{17}ClN_2$: Theory: C, 75.78; H, 5.15; N, 8.42. Found: C, 75.99; H, 5.24; N, 8.43.

The following compounds were synthesized essentially as described in Example 56 by reacting 2-(3-methylphenyl) benzimidazole with the appropriately substituted benzyl halide.

EXAMPLE 57
1-(3-Chlorobenzyl)-2-(3-methylphenyl)benzimidazole.
MS 332, 334, mp 90° C.
Analysis for $C_{21}H_{17}ClN_2$: Theory: C, 75.78; H, 5.15; N, 8.42. Found: C, 75.51; H, 5.20; N, 8.56.

EXAMPLE 58
1-(4-Chlorobenzyl)-2-(3-methylphenyl)benzimidazole.
MS 332, 334, mp 108.5° C.
Analysis for $C_{21}H_{17}ClN_2$: Theory: C, 75.78; H, 5.15; N, 8.42. Found: C, 75.55; H, 5.29; N, 8.37.

EXAMPLE 60
1-(2-Bromobenzyl)-2-(3-methylphenyl)benzimidazole.
MS 376, 378, mp 134° C.
Analysis for $C_{21}H_{17}BrN_2$: Theory: C, 66.85; H, 4.54; N, 7.42. Found: C, 67.13; H, 4.60; N, 7.34.

EXAMPLE 61
1-(2-Iodobenzyl)-2-(3-methylphenyl)benzimidazole.
MS 424, 425, mp 129° C.
Analysis for $C_{21}H_{17}IN_2 \cdot 0.1$ hexanes: Theory: C, 59.93; H, 4.28; N, 6.47. Found: C, 60.20; H, 4.12; N, 6.87.

EXAMPLE 62
1-(2,6-Dichlorobenzyl)-2-(3-methylphenyl)benzimidazole.
mp 148° C., NMR, IR, MS 366, 368.
Analysis for $C_{21}H_{16}Cl_2N_2 \cdot 0.1$ hexanes: Theory: C, 69.02; H, 4.67; N, 7.45. Found: C, 69.25; H, 4.42; N, 7.21.

EXAMPLE 63
1-(2,4-Dichlorobenzyl)-2-(3-methylphenyl)benzimidazole.
mp 161° C., MS 366, 368, IR, NMR.
Analysis for $C_{21}H_{16}Cl_2N_2$: Theory: C, 68.68; H, 4.39; N, 7.63. Found: C, 68.48; H, 4.61; N, 7.70.

EXAMPLE 64
1-(3,4-Dichlorobenzyl)-2-(3-methylphenyl)benzimidazole.
mp 85.5° C., MS 366, 368, IR, NMR.
Analysis for $C_{21}H_{16}Cl_2N_2$: Theory: C, 68.68; H, 4.39; N, 7.63. Found: C, 68.88; H, 4.41; N, 7.50.

EXAMPLE 65
1-(3-Methoxybenzyl)-2-(3-methylphenyl)benzimidazole.

Oil at room temperature. NMR, IR, MS 328.

Analysis for $C_{22}H_{20}N_2O$: Theory: C, 80.46; H, 6.14; N, 8.53. Found: C, 81.39; H, 6.70; N, 8.23.

EXAMPLE 66
1-(4-Methoxybenzyl)-2-(3-methylphenyl)benzimidazole.

mp 91° C., NMR, IR, MS 328.

Analysis for $C_{22}H_{20}N_2O$: Theory: C, 80.46; H, 6.14; N, 8.53. Found: C, 80.68; H, 6.31; N, 8.63.

EXAMPLE 67
Synthesis of 1-(3-hydroxybenzyl)-2-(3-methylphenyl)benzimidazole hydrobromide.

This compound was prepared by first synthesizing 1-(3-methoxybenzyl)-2-(3-methylphenyl)benzimidazole as described in Example 65, supra. With an amount of the compound of Example 65 (4.31 g, 13.12 mmol) in glacial acetic acid (50 ml) and hydrobromic acid (300 ml of a 48% w/v in acetic acid solution). This mixture was stirred for 2 hours while warming to reflux. The mixture was then stirred at reflux for about three hours.

The reaction mixture was then allowed to cool to room temperature after which time the reaction mixture was partitioned between water (1 liter) and methylene chloride, followed by extraction with methylene chloride (3×500 ml). The organic fractions were combined and dried over magnesium sulfate. After reducing the volume of the organic solvents in vacuo, the organic fraction was washed with water (3×250 ml) to remove residual hydrobromic acid. The organic phases were combined and dried in vacuo to yield a gray solid which was washed with diethyl ether (2×250 ml) and dried in a vacuum oven. NMR, IR, MS 314, mp 235° C.

Analysis for $C_{21}H_{18}N_2O$ . HBr: Theory: C, 63.81; H, 4.84; N, 7.09. Found: C, 64.45; H, 5.02; N, 7.23.

EXAMPLE 69
Synthesis of 1-benzyl-2-(3,4,5-trimethoxyphenyl)-6-(hydroxy)-benzimidazole hydrochloride.

The title compound was prepared by first reacting 4-amino-3-nitrophenol (25.0 g, 162.2 mmol) with 3,4,5-trimethoxybenzoyl chloride (112 g, 485.6 mmol) in N,N-diethylaniline (69 ml) and toluene (500 ml). The reaction mixture was stirred and the temperature was raised to 100° C. The solution was maintained at this temperature for about 6 hours as a yellow precipitate formed. The reaction mixture was then partitioned between 1N hydrochloric acid (250 ml) and ethyl acetate (250 ml). The crystals were then removed by filtration and washed with ethyl acetate (300 ml) and water (300 ml) to yield the intermediate 1-(3,4,5-trimethoxy)benzyl ester of 4-(3,4,5-trimethoxyphenylcarbonylamino)-2-nitrophenol.

A benzyl group was then substituted on the nitro group by reacting the above intermediate (10 g, 18.4 mmol) with benzaldehyde (6 ml) in N,N-dimethylformamide (100 ml) under a hydrogen atmosphere (60° C. at 60 p.s.i.) with 6.0 g of a palladium on activated carbon catalyst.

The benzimidazole ring was closed using phosphorous oxychloride in chloroform as described supra. The ester on the 6-hydroxy group of the benzimidazole was removed by incubating the intermediate in 1N sodium hydroxide (500 ml) and tetrahydrofuran (500 ml). This solution was stirred overnight, followed by acidification with a sufficient amount of 1 N hydrochloric acid to reduce the pH to 1.0. This solution was then washed with ethyl acetate (2×500 ml). The organic fractions were combined, dried over magnesium sulfate, and the solvents removed in vacuo to yield a brownish/red solid. The title compound was further purified by flash chromatography to yield a grayish solid. MS 390.

Analysis for $C_{23}H_{22}N_2O_4$.HCl: Theory: C, 64.71; H, 5.43; N, 6.56. Found: C, 65.12; H, 5.40; N, 6.63.

EXAMPLE 70
Synthesis of 1-benzyl-2-(3,4,5-trimethoxyphenyl)-6-[2-(4-morpholinyl)ethoxy]benzimidazole.

The title compound was prepared by reacting the compound of Example 69, supra, (0.23 g, 0.59 mmol) with 4-(2-chloroethyl)morpholine hydrochloride (1.10 g, 5.91 mmol) and potassium carbonate (1.63 g, 11.80 mmol) in acetone. The reaction conditions employed were essentially as described for previous alkylations. MS 503.

Analysis for $C_{29}H_{33}N_3O_5$: Theory: C, 69.17; H, 6.60; N, 8.34. Found: C, 69.10; H, 6.70; N, 8.42.

EXAMPLE 71
Synthesis of 1-benzyl-2-(3,4,5-trimethoxyphenyl)-6-[2-(1-piperidinyl)ethoxy]benzimidazole.

The title compound was prepared essentially as described in Example 70 except that 1-(2-chloroethyl)piperidine hydrochloride was employed in place of 4-(2-chloroethyl)morpholine hydrochloride. MS 501.

Analysis for $C_{30}H_{35}N_3O_4$: Theory: C, 71.83; H, 7.03; N, 8,38. Found: C, 71.95; H, 7.27; N, 8.17.

EXAMPLE 72
Synthesis of 1-benzyl-2-(3,4,5-trimethoxyphenyl)-6-[2-(1-pyrroldinyl)ethoxy]benzimidazole.

The title compound was prepared essentially as described in Example 70 except that 1-(2-chloroethyl)pyrrolidine hydrochloride was employed in place of 4-(2-chloroethyl)morpholine hydrochloride. MS 488.

Analysis for $C_{29}H_{33}N_3O_4$: Theory: C, 71.44; H, 6.82; N, 8.62. Found: C, 71.61; H, 7.05; N, 8.87.

EXAMPLE 73
Synthesis of 1-benzyl-2-(3,4,5-trimethoxyphenyl)-6-[2-(1-hexamethyleneiminyl)ethoxy]benzimidazole.

The title compound was prepared essentially as described in Example 70 except that 1-(2-chloroethyl)hexamethyleneimine hydrochloride was employed in place of 4-(2-chloroethyl)morpholine hydrochloride. NMR, IR, MS 515, mp 122.5° C.

Analysis for $C_{31}H_{37}N_3O_4$: Theory: C, 72.21; H, 7.23; N, 8.15. Found: C, 72.18; H, 7.19; N, 8.42.

EXAMPLE 74
Synthesis of 1-benzyl-2-(3,4,5-trimethoxyphenyl)-6-[3-(1-piperidinyl)propoxy]benzimidazole.

The title compound was prepared essentially as described in Example 70 except that 1-(3-chloropropyl)piperidine hydrochloride was employed in place of 4-(2-chloroethyl)morpholine hydrochloride. mp 92° C., NMR, IR, MS 515.

Analysis for $C_{31}H_{37}N_3O_4$: Theory: C, 72.21; H, 7.23; N, 8.15. Found: C, 72.50; H, 7.26; N, 7.90.

EXAMPLE 75
Synthesis of 1-benzyl-2-(3,4,5-trimethoxyphenyl)-6-(3-chloropropoxy)benzimidazole.

The title compound was prepared essentially as described in Example 70 except that 1-chloro-3-iodopropane was employed in place of 4-(2-chloroethyl)morpholine hydrochloride. mp 118.5° C., MS 466, 468, NMR, IR.

Analysis for $C_{26}H_{27}ClN_2O_4$.0.5 $H_2O$: Theory: C, 65.61; H, 5.93; N, 5.89. Found: C, 65.92; H, 5.74; N, 5.91.

EXAMPLE 76

Synthesis of 1-benzyl-2-(3,4,5-trimethoxyphenyl)-6-(2-chloroethoxy)benzimidazole.

The title compound was prepared essentially as described in Example 70 except that 1-bromo-2-chloroethane was employed in place of 4-(2-chloroethyl)morpholine hydrochloride. IR, NMR, MS 452, 454, mp 129° C.

Analysis for $C_{25}H_{25}ClN_2O_4$: Theory: C, 66.30; H, 5.56; N, 6.19. Found: C, 67.33; H, 5.41; N, 6.61.

EXAMPLE 77

Synthesis of 1-benzyl-2-(3,4,5-trimethoxyphenyl)-6-[2-[4-(piperidin-1-yl)piperdin-1-yl]ethoxy]benzimidazole.

The title compound was prepared by reacting the compound of Example 76, supra, (0.45 g, 1.0 mmol) with 4-piperdin-1-yl)piperidine (2.0 g, 11.9 mmol) in the presence of the base N,N-diisopropylethylamine, tetra-n-butylammonium iodide and acetonitrile at 80° C. After incubating overnight at 80° C. the reaction was washed with water (2×500 ml), followed by a wash with a saturated sodium chloride solution (1×500 ml). The organic phase was then dried over potassium carbonate and the solvents were removed in vacuo to yield a light brown oil. The desired product was purified by chromatography and triturated with diethyl ether to yield a light brown powder, which was removed by filtration and washed with diethyl ether to yield the purified title compound. MS 584, 585, NMR, IR, mp 143° C.

Analysis for $C_{35}H_{44}N_4O_4$: Theory: C, 71.89; H, 7.58; N, 9.58. Found: C, 72.11; H, 7.62; N, 9.67.

EXAMPLE 78

Synthesis of 1-benzyl-2-(3,4,5-trimethoxyphenyl)-6-[1-methyl-2-(N,N-dimethylamino)]ethoxy]benzimidazole.

The title compound was prepared by reacting the compound of Example 70, supra, 0.45 g, 1.15 mmol) with 1-methyl-2-dimethylaminoethyl chloride (1.82 g, 11.51 mmol) and potassium chloride (3.18 g, 23.01 mmol) in 100 ml of acetone. The reactants were admixed and then heated to reflux overnight.

After the overnight incubation the reaction mixture was acidified by adding 500 ml of 1N hydrochloric acid and then washed with ethyl acetate (2×250 ml). The aqueous layer was then basified and extracted with ethyl acetate (500 ml). The organic fractions were combined and washed with a saturated sodium chloride solution and dried over potassium carbonate. The solvents were removed in vacuo to yield a yellow oil which was triturated with hexanes, forming a white solid. This was further purified by crystallizing from 10:1 hexanes:ethanol to yield the desired title product. IR, NMR, MS 475, 476, mp 93° C.

Analysis for $C_{28}H_{33}N_3O_4$: Theory: C, 70.71; H, 6.99; N, 8.84. Found: C, 70.93; H, 7.01; N, 8.92.

EXAMPLE 79

Synthesis of 1-benzyl-2-(3,4,5-trimethoxyphenyl)-6-[2-(N,N-dimethylamino)ethoxy]benzimidazole.

The title compound was prepared essentially as described in Example 78, supra, except that 2-dimethylaminoethyl chloride was employed in place of the 1-methyl-2-dimethylaminoethyl chloride. IR, NMR, MS 461, mp 108° C.

Analysis for $C_{27}H_{31}N_3O_4$.0.1 hexanes: Theory: C, 70.51; H, 6.95; N, 8.94. Found: C, 70.98; H, 6.60; N, 8.62.

EXAMPLE 80

Synthesis of 1-benzyl-2-(3,4,5-trimethoxyphenyl)-6-[3-(N,N-dimethylamino)propoxy]benzimidazole.

The title compound was prepared essentially as described in Example 78, supra, except that 3-dimethylaminopropyl chloride was employed in place of the 1-methyl-2-dimethylaminoethyl chloride. IR, NMR, MS 475, mp 112° C.

Analysis for $C_{28}H_{33}N_3O_4$: Theory: C, 70.71; H, 6.99; N, 8.83. Found: C, 70.42; H, 6.97; N, 8.68.

EXAMPLE 81

Synthesis of 1-benzyl-2-(3,4,5-trimethoxyphenyl)-6-[2-(N,N-diisopropylamino)ethoxy]benzimidazole.

The title compound was prepared essentially as described in Example 78, supra, except that 2-diisopropylaminoethyl chloride was employed in place of the 1-methyl-2-dimethylaminoethyl chloride. IR, NMR, MS 517, 518, mp 101° C.

Analysis for $C_{31}H_{39}N_3O_4$: Theory: C, 71.93; H, 7.59; N, 8.12. Found: C, 71.91; H, 7.76; N, 7.98.

EXAMPLE 83

Synthesis of 1-benzyl-2-(3,4,5-trimethoxyphenyl)-6-[2-(4-methyl-1-piperazinyl)ethoxy]benzimidazole.

The title compound was prepared essentially as described in Example 77, supra, employing the compound of Example 76, except that 1-methylpiperazine was employed in place of the 4-(piperdin-1-yl)piperidine. IR, NMR, MS 517, mp 113° C.

Analysis for $C_{30}H_{36}N_4O_4$.0.5 $H_2O$: Theory: C, 68.55; H, 7.09; N, 10.66. Found: C, 68.83; H, 7.19; N, 10.98.

EXAMPLE 84

Synthesis of 1-benzyl-2-(3-methylphenyl)-6-hydroxybenzimidazole

The title compound was prepared essentially as described in Example 69, supra, except that 3-methylbenzoyl chloride (18.8 g, 121.6 mmol) was employed instead of the 3,4,5-trimethoxybenzoyl chloride. MS 314

Analysis for $C_{21}H_{18}N_2O$: Theory: C, 80.23; H, 5.77; N, 8.91. Found: C, 80.10; H, 5.85; N, 8.81.

EXAMPLE 85

Synthesis of 1-benzyl-2-(3-methylphenyl)-6-[2-(1-piperidinyl)ethoxy]benzimidazole The title compound was synthesized by reacting the compound of Example 84, supra, (0.25 g, 0.79 mmol) with 2-(piperdinyl-1-yl)ethyl chloride (17.46 g, 7.9 mmol) in the presence of potassium carbonate (2.20 g, 15.9 mmol) and acetone (150 ml). These contents were added to a flask and refluxed overnight.

After the overnight incubation, the reaction mixture was quenched by adding 0.5 N hydrochloric acid (300 ml) and was washed with ethyl acetate (300 ml). The aqueous layer was basified with 1N sodium hydroxide until the pH=10. This aqueous layer was extracted with ethyl acetate (300 ml). The organic fractions were combined and the solvent volume was reduced in vacuo, leaving a yellow oil. Diethyl ether and hexanes were added to this oil and it was then placed at −20° C. until crystals of the title product formed, which were then harvested by filtration. MS 425, 426.

Analysis for $C_{28}H_{31}N_3O$: Theory: C, 79.03; H, 7.34; N, 9.87. Found: C, 78.75; H, 7.47; N, 10.09.

EXAMPLE 86

Synthesis of 1-benzyl-2-(3-methylphenyl)-6-[2-(1-pyrrolidinyl)ethoxy]benzimidazole.

The title product was prepared essentially as described in Example 85, supra, except that 1-(2-chloroethyl)pyrrolidine hydrochloride was employed instead of the 2-(piperdinyl-1-yl)ethyl chloride. MS 411.

Analysis for $C_{27}H_{29}N_3O$: Theory: C, 78.80; H, 7.10; N, 10.21. Found: C, 78.85; H, 7.14; N, 10.08.

EXAMPLE 87

Synthesis of 1-benzyl-2-(3-methylphenyl)-6-[2-(4-morpholinyl)ethoxy]benzimidazole The title product was prepared essentially as described in Example 85, supra, except that 4-(2-chloroethyl)morpholine hydrochloride was employed instead of the 2-(piperdinyl-1-yl)ethyl chloride. MS 427.

Analysis for $C_{27}H_{29}N_3O_2$: Theory: C, 75.85; H, 6.84; N, 9.83. Found: C, 75.75; H, 6.89; N, 9.88.

EXAMPLE 88

Synthesis of 1-benzyl-2-(3-methylphenyl)-6-[2-(N,N-dimethylamino)ethoxy]benzimidazole The title product was prepared essentially as described in Example 85, supra, except that 2-(N,N-dimethylamino)ethyl chloride was employed instead of the 2-(piperdinyl-1-yl) ethyl chloride. MS 385.

Analysis for $C_{25}H_{27}N_3O$: Theory: C, 77.89; H, 7.06; N, 10.90. Found: C, 77.88; H, 7.14; N, 10.74.

EXAMPLE 89

Synthesis of 1-benzyl-2-(3-methylphenyl)-6-[2-(N,N-dibenzylamino)ethoxy]benzimidazole The title product was prepared essentially as described in Example 85, supra, except that 2-(N,N-dibenzylamino)ethyl chloride was employed instead of the 2-(piperdinyl-1-yl) ethyl chloride. MS 537.

Analysis for $C_{37}H_{35}N_3O$: Theory: C, 82.65; H, 6.56; N, 7.82. Found: C, 82.47; H, 6.73; N, 7.81.

EXAMPLE 90

Synthesis of 1-benzyl-2-(3-methylphenyl)-6-[2-(N-phenyl-N-ethylamino)ethoxy]benzimidazole The title product was prepared essentially as described in Example 85, supra, except that 2-(N-benzyl-N-ethylamino) ethyl chloride was employed instead of the 2-(piperdinyl-1-yl)ethyl chloride. Ms 461, 462.

Analysis for $C_{31}H_{31}N_3O$: Theory: C, 80.66; H, 6.77; N, 9.10. Found. C, 80.37; H, 6.81; N, 8.98.

EXAMPLE 91

Synthesis of 1-benzyl-2-(3-methylphenyl)-6-[2-(N,N-isopropylamino)ethoxy]benzimidazole The title product was prepared essentially as described in Example 85, supra, except that 2-(N,N-diisopropylamino) ethyl chloride was employed instead of the 2-(piperdinyl-1-yl)ethyl chloride. MS 441.

Analysis for $C_{29}H_{35}N_3O$: Theory: C, 78.87; H, 7.99; N, 5.51. Found: C, 79.07; H, 8.12; N, 5.60.

EXAMPLE 92

Synthesis of 1-benzyl-2-(3-methylphenyl)-6-[2-(hexamethyleneimin-1-yl)ethoxy]benzimidazole The title product was prepared essentially as described in Example 85, supra, except that 2-(hexamethyleneimin-1-yl) ethyl chloride was employed instead of the 2-(piperdinyl-1-yl)ethyl chloride. MS 439.

Analysis for $C_{29}H_{33}N_3O$: Theory: C, 79.23; H, 7.57; N, 9.56. Found: C, 79.45; H, 7.72; N, 9.66.

EXAMPLE 93

Synthesis of 1-benzyl-2-(3-methylphenyl)-6-[2-(N,N-diethylamino)ethoxy]-benzimidazole The title product was prepared essentially as described in Example 85, supra, except that 2-(N,N-diethylamino)ethyl chloride was employed instead of the 2-(piperdinyl-1-yl) ethyl chloride. MS 413, 414.

Analysis for $C_{27}H_{31}N_3O \cdot 0.25 H_2O$: Theory: C, 77.57; H, 7.59; N, 10.05. Found: C, 77.60; H, 7.42; N, 9.74.

EXAMPLE 94

Synthesis of 1-benzyl-2-(3-methylphenyl)-6-[3-(N,N-dimethylamino)propoxy]benzimidazole The title product was prepared essentially as described in Example 85, supra, except that 3-(N,N-dimethylamino) propyl chloride was employed instead of the 2-(piperdinyl-1-yl)ethyl chloride. MS 399.

Analysis for $C_{26}H_{29}N_3O$: Theory: C, 78.16; H, 7.32; N, 10.52. Found: C, 77.93; H, 7.32; N, 10.25.

EXAMPLE 95

Synthesis of 1-benzyl-2-(3-methylphenyl)-6-[3-(piperdin-1-yl)propoxy]-benzimidazole.

The title product was prepared essentially as described in Example 85, supra, except that 3-(piperidin-1-yl)propyl chloride was employed instead of the 2-(piperdinyl-1-yl) ethyl chloride. mp 84° C., MS 439, NMR, IR.

Analysis for $C_{29}H_{33}N_3O$: Theory: C, 79.23; H, 7.57; N, 9.55. Found: C, 79.39; H, 7.59; N, 9.59.

EXAMPLE 96

Synthesis of 1-benzyl-2-(3-methylphenyl)-6-[2-(N,N-dimethylamino)propoxy]-benzimidazole The title product was prepared essentially as described in Example 85, supra, except that 2-(N,N-dimethylamino) propyl chloride was employed instead of the 2-(piperdinyl-1-yl)ethyl chloride. mp 74° C., NMR, IR, MS 399, 400.

Analysis for $C_{26}H_{29}N_3O$: Theory: C, 78.16; H, 7.32; N, 10.52. Found: C, 79.58; H, 7.44; N, 10.49.

EXAMPLE 97

Synthesis of 1-benzyl-2-(3-methylphenyl)-6-(3-chloropropoxy)-benzimidazole

The title product was prepared essentially as described in Example 85, supra, except that 3-chloropropyl iodide was employed instead of the 2-(piperdinyl-1-yl)ethyl chloride. mp 97° C., NMR, IR, MS 390, 391.

Analysis for $C_{24}H_{23}ClN_2O$: Theory: C, 73.74; H, 5.93; N, 7.17. Found: C, 73.61; H, 5.94; N, 7.39.

EXAMPLE 98

Synthesis of 1-benzyl-2-(3-methylphenyl)-6-(2-chloroethoxy)-benzimidazole

The title product was prepared essentially as described in Example 85, supra, except that 2-chloroethyl bromide was employed instead of the 2-(piperdinyl-1-yl)ethyl chloride. mp 88° C., MS 376, 378, NMR, IR.

Analysis for $C_{23}H_{21}ClN_2O$: Theory: C, 73.30; H, 5.62; N, 7.43. Found: C, 73.04; H, 5.67; N, 7.65.

EXAMPLE 99

Synthesis of 1-benzyl-2-(3-methylphenyl)-6-[3-(morpholin-4-yl)propoxy)benzimidazole.

The title compound was prepared by first adding morpholine (1.02 g, 11.77 mmol) and the compound of Example 97, supra, (0.39 g, 1.00 mmol) to 125 ml of acetonitrile while stirring under nitrogen purge. To this mixture is then added diisopropylethyl aniline (1.51 ml, 8.67 mmol) dropwise. This reaction mixture is then allowed to stir overnight.

After the overnight stirring, additional diisopropyl aniline (1.00 ml) is added and the mixture is then heated to 60° C. and maintained at this temperature for about 3 days. The reaction mixture was then washed with water (3×250 ml) and the solvents were removed in vacuo, resulting in a yellow oil.

The yellow oil was further purified by chromatography using ethyl acetate, followed by removal of the solvents in vacuo, and trituration with hexanes to afford yellow crystals. NMR, MS 441, IR, mp 120° C.

Analysis for $C_{28}H_{31}N_3O_2$: Theory: C, 76.16; H, 7.08; N, 9.52. Found: C, 76.39; H, 7.26; N, 9.54.

EXAMPLE 100
Synthesis of 1-benzyl-2-(3-methylphenyl)-6-[3-(pyrrolidin-1-yl)propoxy)benzimidazole The title compound was prepared essentially as described in Example 99, supra, except that pyrrolidine was employed in place of morpholine. mp 120° C., NMR, IR, MS 425.

Analysis for $C_{28}H_{31}N_3O$: Theory: C, 79.03; H, 7.34; N, 9.87. Found: C, 79.22; H, 7.39; N, 9.83.

EXAMPLE 101
Synthesis of 1-benzyl-2-(3-methylphenyl)-6-[3-hexamethyleneimin-1-yl)propoxy)benzimidazole The title compound was prepared essentially as described in Example 99, supra, except that hexamethyleneimine was employed in place of morpholine. mp 69.5° C., NMR, IR, MS 453, 454.

Analysis for $C_{30}H_{35}N_3O$: Theory: C, 79.43; H, 7.78; N, 9.26. Found: C, 79.60; H, 7.88; N, 9.28.

EXAMPLE 102
Synthesis of 1-benzyl-2-(3-methylphenyl)-6-[3-(heptamethyleneimin-1-yl)propoxy)benzimidazole The title compound was by reacting the compound of Example 97, supra, (0.39 g, 1.00 mmol) with heptamethyleneimine (10 g, 88.3 mmol) in the presence of N,N-diisopropylethylamine (2 ml) and acetonitrile (5 ml). This reaction mixture was raised to 80° C. and allowed to stir at that temperature overnight. The compound was purified essentially as described in Example 99, supra. NMR, MS 467, mp 77° C.

Analysis for $C_{31}H_{37}N_3O$: Theory: C, 79.62; H, 7.97; N, 8.98. Found: C, 79.50; H, 7.99; N, 8.99.

EXAMPLE 103
Synthesis of 1-benzyl-2-(3-methylphenyl)-6-[2-(4-methyl-piperazin-1-yl)ethoxy]benzimidazole The title compound was prepared by reacting the compound of Example 98, supra, (1.89 g, 5.01 mmol) with 1-methyl-piperazine (65 ml) in the presence of N,N-diisopropylethyl amine (4 ml) and N,N-dimethylformamide (100 ml) under nitrogen atmosphere. This reaction mixture was heated to 50° C. and stirred overnight at that temperature. The compound was purified essentially as described in Example 99, supra. NMR, IR, MS 440, 441, mp 91° C.

Analysis for $C_{28}H_{32}N_4O$: Theory: C, 76.33; H, 7.32; N, 12.72. Found: C, 76.19; H, 7.15; N, 12.96.

EXAMPLE 104
Synthesis of 1-(2-trifluoromethylbenzyl)-2-(3,4,5-trimethoxyphenyl)-6-hydroxybenzimidazole The title compound was prepared by first reacting 3,4,5-trimethoxybenzoyl chloride (112.0 g, 485.6 mmol) with 4-amino-3-nitrophenol (25.0 g, 162.2 mmol) in N,N-diethylaniline (69 ml) and toluene (500 ml). This reaction mixture was heated to 100° C. and maintained at that temperature for about 6 hours. The intermediate ester of 4-(3,4,5-trimethoxyphenylcarbonylamino)-3-nitrophenol was purified essentially as described in Example 69, supra.

The nitro moiety of the above-described intermediate was reduced to an amino group by catalytic hydrogenation using a palladium on activated carbon catalyst as described previously. This primary amino group was then alkylated by reacting with 2-trifluoromethylbenzyl bromide in the presence of N,N-diisopropylethyl amine and tetrahydrofuran. This mixture was allowed to reflux overnight.

The reaction mixture was then washed with water (5×500 ml) followed by a wash with saturated sodium chloride (500 ml). The organic phase was dried over potassium carbonate, and the solvents were removed in vacuo, leaving a brown solid. Following trituration in diethyl ether a gray solid formed.

The benzimidazole ring was closed using phosphorous oxychloride in chloroform as previously described. The protecting ester on the 6-hydroxy of the benzimidazole ring was removed by incubating the protected compound in 1N sodium hydroxide in tetrahydrofuran to cleave this group, leaving the title compound. NMR, IR, MS 458, mp 191° C.

Analysis for $C_{24}H_{21}F_3N_2O_4$: Theory: C, 62.88; H, 4.62; N, 6.11. Found: C, 62.89; H, 4.88; N, 5.90.

EXAMPLE 105
Synthesis of 1-(2-trifluoromethylbenzyl)-2-(3,4,5-trimethoxyphenyl)-6-[2-(piperidin-1-yl)ethoxy]benzimidazole The title compound was prepared by reacting the compound of Example 104 with 1-(2-chloroethyl)piperidine hydrochloride essentially as previously described. mp 167° C., NMR, IR, MS 570.

Analysis for $C_{31}H_{34}F_3N_3O_4$: Theory: C, 65.37; H, 6.02; N, 7.38. Found: C, 65.40; H, 6.02; N, 7.41.

EXAMPLE 106
Synthesis of 1-(2-trifluoromethylbenzyl)-2-(3,4,5-trimethoxyphenyl)-6-[2-(N,N-dimethylamino)propoxy]-benzimidazole The title compound was prepared by reacting the compound of Example 104 with 2-(N,N-dimethylamino)propyl chloride essentially as previously described. mp 163° C., NMR, IR, MS 543, 544.

Analysis for $C_{29}H_{32}F_3N_3O_4$: Theory: C, 64.08; H, 5.93; N, 7.73. Found: C, 64.00; H, 5.86; N, 7.68.

EXAMPLE 107
Synthesis of 1-(2-trifluoromethylbenzyl)-2-(3,4,5-trimethoxyphenyl)-6-[2-(N,N-dimethylamino)ethoxy]-benzimidazole The title compound was prepared by reacting the compound of Example 104 with 2-(N,N-dimethylamino)ethyl chloride essentially as previously described. mp 151° C., NMR, IR, MS 529.

Analysis for $C_{28}H_{30}F_3N_3O_4$: Theory: C, 63.51; H, 5.71; N, 7.94. Found: C, 63.79; H, 5.57; N, 8.02.

EXAMPLE 108
Synthesis of 1-(2-trifluoromethylbenzyl)-2-(3,4,5-trimethoxyphenyl)-6-[3-(N,N-dimethylamino)propoxy]-benzimidazole The title compound was prepared by reacting the compound of Example 104 with 3-(N,N-dimethylamino)propyl chloride essentially as previously described. mp 142° C., NMR, IR, MS 543.

Analysis for $C_{29}H_{32}F_3N_3O_4$: Theory: C, 64.08; H, 5.93; N, 7.73. Found: C, 64.33; H, 5.78; N, 7.47.

EXAMPLE 109
Synthesis of 1-(2-trifluoromethylbenzyl)-2-(3,4,5-trimethoxyphenyl)-6-[3-(piperidin-1-yl)propoxy]benzimidazole The title compound was prepared by reacting the compound of Example 104 with 3-(piperidin-1-yl)propyl chloride essentially as previously described mp 138° C., IR, NMR, MS. 584

Analysis for $C_{32}H_{36}F_3N_3O_4$: Theory: C, 65.85; H, 6.22; N, 7.20. Found: C, 65.74; H, 6.07; N, 7.35.

EXAMPLE 110
Synthesis of 1-(2-trifluoromethylbenzyl)-2-(3,4,5-trimethoxyphenyl)-6-[2-(hexamethyleneimin-1-yl)ethoxy]benzimidazole The title compound was prepared by reacting the compound of Example 104 with 2-(hexamethyleneimin-1-yl)ethyl chloride essentially as previously described. mp 156° C., IR, NMR, MS 583, 584.

Analysis for $C_{32}H_{36}F_3N_3O_4$: Theory: C, 65.85; H, 6.22; N, 7.20. Found: C, 65.59; H, 5.98; N, 7.33.

EXAMPLE 111
Synthesis of 1-(2-trifluoromethylbenzyl)-2-(3,4,5-trimethoxyphenyl)-6-[2-(pyrrolidin-1-yl)ethoxy]benzimidazole The title compound was prepared by reacting the compound of Example 104 with 2-(pyrrolidin-1-yl)ethyl chloride essentially as previously described. mp 143° C., NMR, IR, MS 555.

Analysis for $C_{30}H_{32}F_3N_3O_4$: Theory: C, 64.85; H, 5.80; N, 7.56. Found: C, 64.93; H, 5.87; N, 7.54.

EXAMPLE 112
Synthesis of 1-(2-trifluoromethylbenzyl)-2-(3,4,5-trimethoxyphenyl)-6-[2-(morpholin-4-yl)ethoxy]benzimidazole The title compound was prepared by reacting the compound of Example 104 with 2-(morpholin-4-yl)ethyl chloride essentially as previously described. mp 175° C., NMR, IR, MS 572.

Analysis for $C_{30}H_{32}F_3N_3O_5$: Theory: C, 63.04; H, 5.64; N, 7.35. Found: C, 62.82; H, 5.74; N, 7.38.

EXAMPLE 113
Synthesis of 1-(2-trifluoromethylbenzyl)-2-(3,4,5-trimethoxyphenyl)-6-[2-(N,N-diisopropylamino)ethoxy]-benzimidazole The title compound was prepared by reacting the compound of Example 104 with 2-(N,N-diisopropylamino)ethyl chloride essentially as previously described. mp 184° C., MS 585, NMR, IR.

Analysis for $C_{32}H_{38}F_3N_3O_4$: Theory: C, 65.63; H, 6.54; N, 7.18. Found: C, 65.67; H, 6.42; N, 7.35.

EXAMPLE 114
Synthesis of 1-(2-bromobenzyl)-2-(3,4,5-trimethoxyphenyl)-6-hydroxybenzimidazole The title compound was prepared essentially as described in Example 104 except that 2-bromobenzyl bromide was employed in place of 2-trifluoromethylbenzyl bromide. mp 208° C., NMR, IR, MS 468, 470.

Analysis for $C_{23}H_{21}BrN_2O_4$: Theory: C, 58.86; H, 4.51; N, 5.97. Found: C, 58.61; H, 4.81; N, 6.12.

EXAMPLE 115
Synthesis of 1-(2-bromobenzyl)-2-(3,4,5-trimethoxyphenyl)-6-[2-(piperidin-1-yl)ethoxy]benzimidazole The title compound was prepared by reacting the compound of Example 114 with 2-(piperidin-1-yl)ethyl chloride essentially as previously described mp 145° C., NMR, MS 579, 581, IR.

Analysis for $C_{30}H_{34}BrN_3O_4$: Theory: C, 62.07; H, 5.90; N, 7.24. Found: C, 61.86; H, 5.91; N, 7.08.

EXAMPLE 116
Synthesis of 1-(2-bromobenzyl)-2-(3,4,5-trimethoxyphenyl)-6-[2-(N,N-dimethylamino)propoxy]benzimidazole The title compound was prepared by reacting the compound of Example 114 with 2-(N,N-dimethylamino)propyl chloride essentially as previously described. mp 152° C., NMR, IR, MS 553, 555.

Analysis for $C_{28}H_{32}BrN_3O_4$: Theory: C, 60.65; H, 5.82; N, 7.58. Found: C, 60.85; H, 5.77; N, 7.44.

EXAMPLE 117
Synthesis of 1-(2-bromobenzyl)-2-(3,4,5-trimethoxyphenyl)-6-[2-(N,N-dimethylamino)ethoxy]benzimidazole The title compound was prepared by reacting the compound of Example 114 with 2-(N,N-dimethylamino)ethyl chloride essentially as previously described. mp 152° C., NMR, IR, MS 539, 541.

Analysis for $C_{27}H_{30}BrN_3O_4$: Theory: C, 60.00; H, 5.59; N, 7.77. Found: C, 59.83; H, 5.63; N, 7.54.

EXAMPLE 118
Synthesis of 1-(2-bromobenzyl)-2-(3,4,5-trimethoxyphenyl)-6-[3-(N,N-dimethylamino)propoxy]benzimidazole The title compound was prepared by reacting the compound of Example 114 with 3-(N,N-dimethylamino)propyl chloride essentially as previously described mp 141° C., NMR, IR, MS 553, 555.

Analysis for $C_{28}H_{32}BrN_3O_4$: Theory: C, 60.65; H, 5.82; N, 7.58. Found: C, 60.49; H, 6.03; N, 7.34.

EXAMPLE 119
Synthesis of 1-(2-bromobenzyl)-2-(3,4,5-trimethoxyphenyl)-6-[2-(N,N-diisopropylamino)ethoxy]benzimidazole The title compound was prepared by reacting the compound of Example 114 with 2-(N,N-diisopropylamino)ethyl chloride essentially as previously described MS 595, 597.

Analysis for $C_{31}H_{38}BrN_3O_4$: Theory: C, 62.41; H, 6.42; N, 7.04. Found: C, 62.48; H, 6.48; N, 7.03.

EXAMPLE 120
Synthesis of 1-(2-trifluoromethylbenzyl)-2-(3-methylphenyl)-6-hydroxybenzimidazole The title compound was prepared essentially as described in Example 104, supra, except that 3-methylbenzoyl chloride was employed instead of 3,4,5-trimethoxybenzoyl chloride. mp 233° C., MS 382, IR, NMR.

Analysis for $C_{22}H_{17}F_3N_2O$: Theory: C, 69.10; H, 4.48; N, 7.33. Found. C, 69.40; H, 4.49; N, 7.27.

EXAMPLE 121
Synthesis of 1-(2-trifluoromethylbenzyl)-2-(3-methylphenyl)-6-[2-(piperidinyl-1-yl)ethoxy]benzimidazole The title compound was prepared essentially as described in Example 105 except that the compound of Example 120 was reacted with 2-(piperidin-1-yl)ethyl chloride. mp 114° C., NMR, IR, MS 493.

EXAMPLE 122

Synthesis of 1-(2-trifluoromethylbenzyl)-2-(3-methylphenyl)-6-[2-(N,N-dimethylamino)ethoxy]benzimidazole The title compound was prepared essentially as described in Example 107 except that the compound of Example 120 was reacted with 2-(N,N-dimethylamino)ethyl chloride. mp 93° C., NMR, IR, MS 453.

Analysis for $C_{26}H_{26}F_3N_3O$: Theory: C, 68.86; H, 5.78; N, 9.26. Found: C, 69.12; H, 5.79; N, 9.34.

EXAMPLE 123

Synthesis of 1-(2-trifluoromethylbenzyl)-2-(3-methylphenyl)-6-[2-(N,N-diisopropylamino)ethoxy]-benzimidazole The title compound was prepared essentially as described in Example 113 except that the compound of Example 120 was reacted with 2-(N,N-diisopropylamino)ethyl chloride. MS 510.

Analysis for $C_{30}H_{34}F_3N_3O$: Theory: C, 70.71; H, 6.72; N, 8.25. Found: C, 70.48; H, 6.59; N, 8.26.

EXAMPLE 124

Synthesis of 1-(2-trifluoromethylbenzyl)-2-(3-methylphenyl)-6-[3-(N,N-dimethylamino)propoxy]benzimidazole The title compound was prepared essentially as described in Example 106 except that the compound of Example 120 was reacted with 3-(N,N-dimethylamino)propyl chloride. mp 74° C., NMR, IR, MS 468.

Analysis for $C_{27}H_{28}F_3N_3O$: Theory: C, 69.36; H, 6.04; N, 8.99. Found: C, 69.52; H, 6.10; N, 9.03.

EXAMPLE 125

Synthesis of 1-(2-trifluoromethylbenzyl)-2-(3-methylphenyl)-6-[1-methyl-2-(N,N-dimethylamino)ethoxy]-benzimidazole The title compound was prepared essentially as described above except that the compound of Example 120 was reacted with 1-methyl-2-(N,N-dimethylamino)ethyl chloride, yielding the title product as an oil.

EXAMPLE 126

Synthesis of 1-(2-bromobenzyl)-2-(3-methylphenyl)-6-hydroxybenzimidazole

The title compound was prepared essentially as described in Example 114, supra, except that 3-methylbenzoyl chloride was employed instead of 3,4,5-trimethoxybenzoyl chloride. mp 218° C., NMR, IR, MS 392, 394.

Analysis for $C_{21}H_{17}BrN_2O$: Theory: C, 64.13; H, 4.36; N, 7.12. Found: C, 64.23; H, 4.51; N, 6.93.

EXAMPLE 127

Synthesis of 1-(2-bromobenzyl)-2-(3-methylphenyl)-6-[2-(piperidinyl-1-yl)ethoxy]benzimidazole The title compound was prepared essentially as described in Example 115 except that the compound of Example 126 was reacted with 2-(piperidin-1-yl)ethyl chloride. mp 107° C., NMR, IR, MS 503, 505.

Analysis for $C_{28}H_{30}BrN_3O$: Theory: C, 66.67; H, 5.99; N, 8.33. Found: C, 66.97; H, 6.12; N, 8.19.

EXAMPLE 128

Synthesis of 1-(2-bromobenzyl)-2-(3-methylphenyl)-6-[2-(N,N-dimethylamino)ethoxy]benzimidazole The title compound was prepared essentially as described in Example 117 except that the compound of Example 126 was reacted with 2-(N,N-dimethylamino)ethyl chloride. mp 71° C., NMR, IR, MS 464, 466.

Analysis for $C_{25}H_{26}BrN_3O$: Theory: C, 64.66; H, 5.64; N, 9.05. Found: C, 64.58; H, 5.58; N, 9.04.

EXAMPLE 130

Synthesis of 1-(2-bromobenzyl)-2-(3-methylphenyl)-6-[3-(N,N-dimethylamino)propoxy]benzimidazole The title compound was prepared essentially as described in Example 116 except that the compound of Example 126 was reacted with 3-(N,N-dimethylamino)propyl chloride. MS 479.

Analysis for $C_{26}H_{28}BrN_3O$: Theory: C, 65.27; H, 5.90; N, 8.78. Found: C, 64.99; H, 5.85; N, 8.66.

EXAMPLE 131

Synthesis of 1-(2-bromobenzyl)-2-(3-methylphenyl)-6-[1-methyl-2-(N,N-dimethylamino)ethoxy]benzimidazole The title compound was prepared essentially as described above except that the compound of Example 126 was reacted with 1-methyl-2-(N,N-dimethylamino)ethyl chloride.

EXAMPLE 132

Synthesis of 1-(2-trifluoromethylbenzyl)-2-(3,4-dimethylphenyl)-6-hydroxybenzimidazole The title compound was prepared essentially as described in Example 104 except that 3,4,dimethylbenzoyl chloride was employed instead of 3,4,5-trimethoxybenzoyl chloride. mp 178° C., NMR, IR, MS 396.

Analysis for $C_{23}H_{19}F_3N_2O$: Theory: C, 69.69; H, 4.83; N, 7.07. Found: C, 69.40; H, 4.87; N, 6.90.

The following compounds were prepared essentially as described supra, except that the compound of Example 132 was employed as a starting material.

EXAMPLE 133

1-(2-trifluoromethylbenzyl)-2-(3,4-dimethylphenyl)-6-[2-(piperidin-1-yl)ethoxy]benzimidazole. mp 131° C., NMR, MS 507, IR.

Analysis for $C_{30}H_{32}F_3N_3O$: Theory: C, 70.99; H, 6.35; N, 8.28. Found: C, 70.70; H, 6.23; N, 8.42.

EXAMPLE 134

1-(2-trifluoromethylbenzyl)-2-(3,4-dimethylphenyl)-6-[2-(N,N-dimethylamino)ethoxy]benzimidazole. mp 87° C., MS 467, NMR, IR.

Analysis for $C_{27}H_{28}F_3N_3O$: Theory: C, 69.36; H, 6.04; N, 8.99. Found: C, 69.42; H, 6.01; N, 8.91.

EXAMPLE 135

1-(2-trifluoromethylbenzyl)-2-(3,4-dimethylphenyl)-6-[2-(N,N-diisopropylamino)ethoxy]benzimidazole. mp 121° C., NMR, IR, MS 524.

Analysis for $C_{31}H_{36}F_3N_3O$: Theory: C, 71.11; H, 6.93; N, 8.03. Found: C, 71.34; H, 6.96; N, 8.26.

EXAMPLE 136

1-(2-trifluoromethylbenzyl)-2-(3,4-dimethylphenyl)-6-[2-(N,N-dimethylamino)propoxy]benzimidazole. MS 481.

Analysis for $C_{28}H_{30}F_3N_3O$: Theory: C, 69.84; H, 6.28; N, 8.73. Found: C, 70.24; H, 6.33; N, 8.55.

EXAMPLE 136A
1-(2-trifluoromethylbenzyl)-2-(3,4-dimethylphenyl)-6-[1-methyl-2-(N,N-dimethylamino)ethoxy]benzimidazole

MS 481.

Analysis for $C_{28}H_{30}F_3N_3O$: Theory: C, 69.84; H, 6.28; N, 8.73. Found: C, 69.61; H, 6.35; N, 8.50.

EXAMPLE 137
1-(2-bromomethylbenzyl)-2-(3,4-dimethylphenyl)-6-hydroxybenzimidazole The title compound was prepared essentially as described in Example 114, supra, except that 3,4-dimethylbenzoyl chloride was employed instead of 3,4,5-trimethoxybenzoyl chloride. mp 213° C., MS 406, 408, NMR, IR.

Analysis for $C_{22}H_{19}BrN_2O$: Theory: C, 64.56; H, 5.17; N, 6.84. Found: C, 64.76; H, 4.95; N, 6.62.

The following compounds were prepared essentially as described supra, except that the compound of Example 138 was employed as a starting material.

EXAMPLE 138
1-(2-trifluoromethylbenzyl)-2-(3,4-dimethylphenyl)-6-[3-(N,N-dimethylamino)propoxy]benzimidazole Analysis for $C_{27}H_{30}BrN_3O$: Theory: C, 65.85; H, 6.14; N, 8.53. Found: C, 66.12; H, 6.20; N, 8.49.

EXAMPLE 139
1-(2-bromobenzyl)-2-(3,4-dimethylphenyl)-6-[2-(piperidin-1-yl)ethoxy]benzimidazole. mp 137° C., NMR, IR, MS 517, 519.

Analysis for $C_{29}H_{32}BrN_3O$: Theory: C, 67.18; H, 6.72; N, 8.10. Found: C, 67.45; H, 6.30; N, 8.01.

EXAMPLE 140
1-(2-bromobenzyl)-2-(3,4-dimethylphenyl)-6-[2-(N,N-dimethylamino)ethoxy]benzimidazole. mp 102° C., IR, NMR, MS 478, 479, 480.

Analysis for $C_{26}H_{28}BrN_3O$: Theory: C, 65.27; H, 5.90; N, 8.78. Found: C, 65.43; H, 5.88; N, 8.75.

EXAMPLE 141
1-(2-bromobenzyl)-2-(3,4-dimethylphenyl)-6-[2-(N,N-diisopropylamino)ethoxy]benzimidazole

MS 533, 535.

Analysis for $C_{30}H_{36}BrN_3O$: Theory: C, 67.41; H, 6.79; N, 7.86. Found: C, 67.36; H, 6.60; N, 7.93.

EXAMPLE 142
1-(2-bromobenzyl)-2-(3,4-dimethylphenyl)-6-[2-(N,N-dimethylamino)propoxy]benzimidazole. MS 491, 493.

Analysis for $C_{27}H_{30}BrN_3O$: Theory: C, 65.85; H, 6.14; N, 8.53. Found: C, 66.07; H, 6.18; N, 8.54.

EXAMPLE 142A
1-(2-bromobenzyl)-2-(3,4-dimethylphenyl)-6-[1-methyl-2-(N,N-dimethylamino)ethoxy]benzimidazole. MS 491, 493.

Analysis for $C_{27}H_{30}BrN_3O$: Theory: C, 65.85; H, 6.14; N, 8.53. Found: C, 65.74; H, 6.20; N, 8.32.

EXAMPLE 143
1-(2-bromobenzyl)-2-(3,4-dimethylphenyl)-6-[3-(N,N-dimethylamino)propoxy]benzimidazole. MS 491, 493.

Analysis for $C_{11}H_{14}N_2O_4S$: Theory: C, 65.85; H, 6.14; N, 8.53. Found: C, 66.12; H, 6.20; N, 8.49.

EXAMPLE 145
1-(2-bromomethylbenzyl)-2-(3,5-dimethylphenyl)-6-hydroxybenzimidazole The title compound was prepared essentially as described in Example 114, supra, except that 3,5-dimethylbenzoyl chloride was employed instead of 3,4,5-trimethoxybenzoyl chloride. mp 213° C., MS 406, 408, NMR, IR.

Analysis for $C_{22}H_{19}BrN_2O$: Theory: C, 64.88; H, 4.70; N, 6.88. Found: C, 64.74; H, 4.80; N, 7.01.

The following compounds were prepared essentially as described supra, except that the compound of Example 145 was employed as a starting material.

EXAMPLE 146
1-(2-bromobenzyl)-2-(3,5-dimethylphenyl)-6-[2-(piperidin 1-yl)ethoxy]benzimidazole IR, NMR, MS 517, 519, mp 112° C.

Analysis for $C_{29}H_{32}BrN_3.0.5\ H_2O$: Theory: C, 66.03; H, 6.31; N, 7.97. Found: C, 66.17; H, 6.50; N, 7.46.

EXAMPLE 147
1-(2-bromobenzyl)-2-(3,5-dimethylphenyl)-6-[2-(N,N-dimethylamino)ethoxy]benzimidazole

MS 477, 479.

Analysis for $C_{26}H_{28}BrN_3O \cdot H_2O$: Theory: C, 62.90; H, 6.09; N, 8.46. Found: C, 63.09; H, 5.95; N, 8.45.

EXAMPLE 148
1-(2-bromobenzyl)-2-(3,5-dimethylphenyl)-6-[1-methyl-2-(N,N-dimethylamino)ethoxy]benzimidazole. mp 78° C., NMR, IR, MS 491, 493.

Analysis for $C_{27}H_{30}BrN_3O$: Theory: C, 65.85; H, 6.14; N, 8.53. Found: C, 66.05; H, 6.15; N, 8.80.

EXAMPLE 149
1-(2-bromobenzyl)-2-(3,5-dimethylphenyl)-6-[2-(N,N-diisopropylamino)ethoxy]benzimidazole

MS 534, 536.

Analysis for $C_{30}H_{36}BrN_3O$: Theory: C, 67.41; H, 6.79; N, 7.86. Found: C, 67.34; H, 6.87; N, 7.62.

EXAMPLE 150
1-(2-bromobenzyl)-2-(3,5-dimethylphenyl)-6-[3-(N,N-dimethylamino)propoxy]benzimidazole. MS 491, 493.

Analysis for $C_{27}H_{30}BrN_3O$: Theory: C, 65.85; H, 6.14; N, 8.53. Found: C, 65.68; H, 6.19; N, 8.53.

EXAMPLE 151
1-phenyl-2-[3-[2-piperidin-1-yl)ethoxy]phenyl]-benzimidazole

The title compound was prepared by reacting the compound of Example 34 with 2-(piperdin-1-yl)ethyl chloride in acetone and potassium carbonate as previously described. mp 68° C., IR, NMR, MS 397.

Analysis for $C_{26}H_{27}N_3O$: Theory: C, 78.56; H, 6.85; N, 10.57. Found: C, 78.41; H, 6.90; N, 10.45.

EXAMPLE 152
1-phenyl-2-[4-[2-(piperidin-1-yl)ethoxy]phenyl]-benzimidazole

The title compound was prepared by reacting the compound of Example 29 with 2-(piperdin-1-yl)ethyl chloride in acetone and potassium carbonate as previously described. mp 107° C., NMR, MS 397.

Analysis for $C_{26}H_{27}N_3O$: Theory: C, 78.56; H, 6.85; N, 10.57. Found: C, 78.79; H, 7.12; N, 10.51.

EXAMPLE 153
1-phenyl-2-[4-[3-(piperidin-1-yl)propoxy]phenyl]-benzimidazole

The title compound was prepared by reacting the compound of Example 29 with 3-(piperdin-1-yl)propyl chloride in acetone and potassium carbonate as previously described. mp 86° C., NMR, MS 412.

Analysis for $C_{27}H_{29}N_3O$: Theory: C, 78.80; H, 7.10; N, 10.21. Found: C, 79.01; H, 7.18; N, 10.20.

EXAMPLE 154
Synthesis of 1-phenyl-2-(3,4-dimethylphenyl)-6-hydroxybenzimidazole The title compound was prepared by first reacting 1-chloro-3,4-dinitrobenzene (100 g, 0.50 mole) with aniline (140 ml, 1.54 moles) in ethanol (95%, 550 ml). This reaction mixture was stirred at room temperature for about 72 hours. The resulting 1-chloro-3-phenylamino-4-nitrobenzene was purified by first filtering the orange crystals, followed by washing with hexanes. The crystals were then dried at 80° C. for about 4 hours. Additional product was recovered from the hexanes filtrate by recrystallizing from ethanol.

The 1-chloro-3-phenylamino-4-nitrobenzene was then reacted with two molar equivalents of sodium methoxide, the sodium methoxide being prepared essentially as described in Kottenhahn, et al., *Journal of Organic Chemistry* 28:3114 (1963). Metallic sodium (5.0 g, 217 mmol) was added slowly to methanol (400 ml). After all of the sodium had gone into solution, the 1-chloro-3-phenylamino-4-nitrobenzene was added and the red-orange solution was heated to reflux and maintained at that temperature overnight. The gold crystals of 1-methoxy-3-phenylamino-4-nitrobenzene were recovered by filtration, washed with water (2 liters) and dried in vacuo.

The nitro group of the above-described intermediate was then reduce to an amino group by catalytic hydrogenation using a palladium on activated carbon catalyst, essentially as previously described, resulting in 3-phenylamino-4-methoxyaniline with was then reacted with 3,4-dimethylbenzoyl chloride as previously described. This intermediate was then cyclized to the corresponding benzimidazole with phosphorous oxychloride as previously described to yield 1-phenyl-2-(3,4-dimethylphenyl)-6-methoxybenzimidazole.

This intermediate was then reacted with hydrobromic acid (48%) and glacial acetic acid under nitrogen atmosphere to cleave the methoxy group from the 6-position of the benzimidazole. The resulting title compound was purified by adding the reaction mixture to one liter of water and extracting with methylene chloride (3×500 ml). The organic fractions were combined, dried over magnesium sulfate and the solvents were removed in vacuo to yield reddish solid crystals. The crystals were washed with water (3×250 ml) to remove excess hydrobromic acid and then dried, followed by washing with diethyl ether (2×250 ml) and drying in vacuo. mp 251° C., IR, NMR, MS 314.

Analysis for $C_{21}H_{18}N_2O$: Theory: C, 80.23; H, 5.77; N, 8,91. Found: C, 79.98; H, 5.77; N, 8.94.

EXAMPLE 155
1-phenyl-2-(3,4-dimethylphenyl)-6-[2-(piperidin-1-yl)ethoxy]benzimidazole The title compound was prepared by reacting the compound of Example 154, supra, with 2-(piperidin-1-yl)ethyl chloride as previously described. NMR, IR, MS 425, mp 111° C.

Analysis for $C_{28}H_{31}N_3O \cdot 0.5 H_2O$: Theory: C, 77.39; H, 7.42; N, 9.67. Found: C, 77.38; H, 7.24; N, 10.36.

The following compounds were prepared essentially as described above:

EXAMPLE 156
1-Benzyl-2-phenylbenzimidazole

EXAMPLE 157
1-(1-Diethylaminopent-4-yl)-2-(3-nitrophenyl) benzimidazole

EXAMPLE 158
1-(1-Diethylaminopent-4-yl)-2-(4-methoxyphenyl)-benzimidazole

EXAMPLE 159
1-(1-Dimethylaminoethyl)-2-phenylbenzimidazole

EXAMPLE 160
1-(1-Dimethylaminopropyl)-2-benzylbenzimidazole

EXAMPLE 161
1-(4-chlorophenylmethyl)-2-(4-chlorophenylmethyl)-benzimidazole. mp 89–90° C.

EXAMPLE 162
1-phenyl-2-(4-chlorophenyl)-6-methoxybenzimidazole. mp 171–172.5° C.

EXAMPLE 163
1-phenyl-2-(4-chlorophenyl)-5-(1-ethylaminoethyl)-benzimidazole, (Z)-2-butenedioic acid salt. mp 228° C.

EXAMPLE 164
1-phenyl-2-(4-chlorophenyl)-6-chlorobenzimidazole. mp 210–212° C.

EXAMPLE 165
1-phenyl-2-(4-chlorophenyl)-6-(imidazol-1-yl) benzimidazole. mp 223° C.

EXAMPLE 166
1-phenyl-2-(4-chlorophenyl)-5-nitrobenzimidazole. mp 194° C.

EXAMPLE 167
1-phenyl-2-(4-chlorophenyl)-6-hydroxyethylamino-benzimidazole. mp 225° C.

EXAMPLE 168
1-phenyl-2-(4-chlorophenyl)-5-(1-aminoethyl) benzimidazole, (Z)-2-butenedioic acid salt. mp 206° C.

EXAMPLE 169
1-phenyl-2-(4-chlorophenyl)-6-(N-isopropylcarbonyl-N-butylamino)benzimidazole. bp 213–220°C.

EXAMPLE 170
1-phenyl-2-(4-chlorophenyl)-5-acetylbenzimidazole. mp 159° C.

EXAMPLE 171
1-phenyl-2-(4-chlorophenyl)-5-(2-hydroxyethyl) benzimidazole. mp 165° C.

EXAMPLE 172
1-phenyl-2-(4-chlorophenyl)-6-[2-(piperidin-1-yl)ethoxy] benzimidazole. mp 138–140.

EXAMPLE 173
1-phenyl-2-(4-chlorophenyl)-6-[3-(N,N-dimethylamino) propoxy]benzimidazole. mp 126° C.

EXAMPLE 174

1-phenyl-2-(4-hydroxyphenyl)-6-hydroxybenzimidazole, hydrochloride. mp 212° C.

The other compounds of Formula I may be prepared essentially as described above, employing corresponding starting materials.

The biological efficacy of a compound believed to be effective as a tachykinin receptor antagonist may be confirmed by employing an initial screening assay which rapidly and accurately measured the binding of the tested compound to known NK-1 and NK-2 receptor sites. Assays useful for evaluating tachykinin receptor antagonists are well known in the art. See. e.g., J. Jukic, et al., *Life Sciences*, 49:1463–1469 (1991); N. Kulcharczyk, et al., *Journal of Medicinal Chemistry*, 36:1654–1661 (1993); N. Rouissi, et al., *Biochemical and Biophysical Research Communications* 176:894–901 (1991).

NK-1 Receptor Binding Assay

Radioreceptor binding assays were performed using a derivative of a previously published protocol. D. G. Payan, et al., *Journal of Immunology*, 133:3260–3265 (1984). In this assay an aliquot of IM9 cells ($1 \times 10^6$ cells/tube in RPMI 1604 medium supplemented with 10% fetal calf serum) was incubated with 20 pM $^{125}$I-labeled substance P in the presence of increasing competitor concentrations for 45 minutes at 4° C.

The IM9 cell line is a well-characterized cell line which is readily available to the public. See. e.g., *Annals of the New York Academy of Science*, 190: 221–234 (1972); *Nature (London)* 251:443–444 (1974); *Proceedings of the National Academy of Sciences (USA)*, 71:84–88 (1974). These cells were routinely cultured in RPMI 1640 supplemented with 50 μg/ml gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

Many of the compounds employed in the methods of the present invention are also effective antagonists of the NK-2 receptor.

NK-2 Receptor Binding Assay

The CHO-hNK-2R cells, a CHO-derived cell line transformed with the human NK-2 receptor, expressing about 400,000 such receptors per cell, were grown in 75 cm² flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure and the final pellets were resuspended in 100–120 ml 50 mM Tris buffer, pH 7.4, and 4 ml aliquots stored frozen at −70° C. The protein concentration of this preparation was 2 mg/ml.

For the receptor binding assay, one 4-ml aliquot of the CHO-hNK-2R membrane preparation was suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) was used per sample. The radioactive ligand was [$^{125}$I]iodohistidyl-neurokinin A (New England Nuclear, NEX-252), 2200 Ci/mmol. The ligand was prepared in assay buffer at 20 nCi per 100 μl; the final concentration in the assay was 20 pM. Non-specific binding was determined using 1 μM eledoisin. Ten concentrations of eledoisin from 0.1 to 1000 nM were used for a standard concentration-response curve.

All samples and standards were added to the incubation in 10 μl dimethylsulfoxide (DMSO) for screening (single dose) or in 5 μl DMSO for $IC_{50}$ determinations. The order of additions for incubation was 190 or 195 μl assay buffer, 200 μl homogenate, 10 or 5 μl sample in DMSO, 100 μl radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 ml of cold 50 mM Tris buffer, pH 7.7. The filter circles were then punched into 12×75 mm polystyrene tubes and counted in a gamma counter.

It has been determined that the method of the present invention is effective in treating mammals, particularly middle-aged women, exhibiting symptoms of interstitial cystitis and/or urethral syndrome. In this regard, the clinical and local immune response to the compounds of the present invention is investigated in an open trail with 10 female interstitial cystitis patients, whose disease is diagnosed according to the consensus criteria developed in 1987 at a National Institutes of Health workshop. To make objective the symptoms and the clinical response of the patients the present inventors scored (scale 0 to 2) the symptoms of frequency, urgency, nocturia, dysuria and suprapubic pain, as described in U.S. Pat. No. 5,145,859, issued Sep. 8, 1992, the entire contents of which are herein incorporated by reference. A compound of the present invention is administered as a single daily dose determined by a dose-titration test. Urinary interleukin-2 inhibitory activity (IL-2-IN), a marker of cell-mediated inflammation, is measured using a murine interleukin-2 dependent cell line.

The patients are reviewed for reduction in clinical symptoms. Drug side-effects are minimal. Urinary IL-2-IN activity before therapy confirms the presence of cell-mediated inflammation: after 4 months of therapy IL-2-IN activity is normal in most of the patients, regardless of the severity of symptoms, which indicates that the compounds of Formula I exerts an immunosuppressive effect. The data suggests that the compounds of Formula I can be an efficacious, well-tolerated, convenient oral medication for the treatment of interstitial cystitis.

In addition, as more clearly demonstrated below in Example 2, the present inventors also observes similar responses in regard to the treatment of urethral syndrome. As a result, the test data clearly indicates that the compounds employed in the present invention can be effective therapeutic agents for the treatment of interstitial cystitis and/or urethral syndrome.

As a result, it has been found that compounds of Formula I are particularly well-suited for the treatment of interstitial cystitis and/or urethral syndrome because they not only provide effective relief, are available for oral administration, and are relatively inexpensive. It has been discovered that patients receiving the compounds of Formula I substantially reduce the pathological conditions exhibited by these two painful bladder disorders, and are able to carry on their daily activities in a relatively normal existence in comparison with their pre-treatment state.

The present invention will be further described according to the following non-limiting examples.

EXAMPLE 1

Materials and Methods

Patients. The diagnosis of interstitial cystitis is assigned to 10 female patients, aged 23 to 51 years, in accordance with the consensus criteria established at the National Institutes of Health workshop on interstitial cystitis, August, 1987 (Gillenwater, J. Y. and Wein, A J.: Summary of the National Institute of Arthritis, Diabetes, Digestive and Kidney Diseases Workshop on Interstitial Cystitis, National Institutes of Health, Bethesda, Md., Aug. 28–29, 1987, J. Urol., 140:203, 1988), and U.S. Pat. No. No. 5,145,859:

Interstitial Cystitis: Criteria for Diagnosis

| Inclusion Criteria | Exclusion Criteria |
|---|---|
| Hunner's Ulcer (if present, automatic inclusion) | less than 18 years old benign or malignant tumors radiation, tuberculous, bacterial |
| Positive Factors (at least 2 required for inclusion): | or cyclophosphamide cystitis vaginitis duration of symptoms <1 year |
| suprapubic, pelvic, urethral, vaginal or perineal pain | gynecologic cancer urethral diverticulum, bladder or lower ureteral calculi |
| glomerulations at cystoscopy after bladder distension (80 cm water pressure × 1 min.) | active herpes (HSV II) waking frequency <5 in 12 hrs. nocturia <2 neurogenic bladder dysfunction |
| decreased compliance on cystometrogram | waking capacity >400 ml, absence of urgency with bladder filling symptoms relieved by antibiotics, urinary |
| pain on bladder filling relieved by emptying | urinary analgesics or antiseptics |

Cystometrics are performed after cessation of other modes of therapy and prior to institution of therapy: all patients had a waking bladder capacity of less than 350 ml (range 150 ml to 340 ml).

Symptom Evaluation: The symptom scores (total score range: 0 to 10) form the basis for the evaluation of treatment efficacy. The severity of each symptom is assigned a numerical value, as follows:

Symptom Severity Survey

| Symptom | Description | Score |
|---|---|---|
| Frequency (daytime) | voids once every 3 to 5 hours | 0 |
| | voids once every 1 to 2 hours | 1 |
| | voids more than once every hour | 2 |
| Urgency | urge to void equal to actual frequency | 0 |
| | urge to void exceeds actual frequency | 1 |
| | constant urge to void | 2 |
| Nocturia | no nocturia, or 1 void nightly | 0 |
| | nocturia 2 to 4 times nightly | 1 |
| | more than 4 times nightly | 2 |
| Dysuria | no dysuria | 0 |

-continued

| Symptom | Description | Score |
|---|---|---|
| | intermittent dysuria | 1 |
| | dysuria with each void | 2 |
| Suprapubic pain (abdomino-perineal) | no pain | 0 |
| | intermittent pain | 1 |
| | constant pain | 2 |

At the time of diagnosis, and before any treatment, any patient who falls within the parameters of the inclusion of exclusion descriptors of the NIH workshop consensus criteria (above) will score at least a "4" on this survey (frequency<1; urgency<1; nocturia<1; and either dysuria or suprapubic pain<1).

Urine Collection: Urine specimens are collected from all patients before and during therapy. Voided urine is centrifuged at 1000×g for 10 minutes at 4° C. and the supernatant separated from the sediment. The urine supernatant is subjected to $0.2\mu$ filtration (celluloseacetate) at 4° C. to remove any bacteria and debris, and a 1 ml aliquot is removed for creatinine measurement (CREATININE II ANALYZER™, Beckman Instruments, Inc., Brea, Calif.). The supernatant is ultrafiltered against 3×volume in phosphate-buffered saline (PBS) with 0.1 $\mu$g/ml albumin (Sigma, St. Louis, Miss.) using a filtration device (5,000 MW cut off, Amicon, Deavers, Mass.). The concentrated supernatant is dialyzed using 3,500 MW cutoff tubing, shell frozen with dry ice, and vacuum lyophilized. The powder is stored at −20° C.

Measurement of IL-2-IN Activity: The bioassay for IL-2-IN is modified from the method for measuring IL-2 activity described by Gillis and associates. S. Gillis, et al., "T-Cell Growth Factor: Parameters Of Production And A Quantitative Microassay For Activity, *Journal of Immunology,* 120:2027, (1978). The murine IL-2-dependent cytotoxic T-cell line (CTLL-N) is derived from the CT-6 cell line. J. Kusugami, et al., "Intestinal Immune Reactivity To Interleukin-2 Differs Among Crohn's Disease, Ulcerative Colitis And Controls", *Gastroenterology* 97:1 (1989). The CTTL-Ns are maintained in liquid culture using a 1:1 mixture of Roswell Park Memorial Institute (RPMI) 1640 and Dulbecco's Modified Eagles Medium (DMEM; 4.5 g/L glucose) media supplemented with 2.9 mg/ml glucose, 9.4 mM HEPES buffer, 1.9 mg/ml glutamine, 289 $\mu$g/ml arginine, 0.12 M non-essential amino acids, $5\times10^{-5}$ M 2-mercaptoethanol, 4.5% fetal bovine serum, 90 units/ml penicillin, 90 $\mu$g/ml streptomycin, 22 $\mu$g/ml fungizone, 0.45 mg/ml gentamicin and 20 units/ml of human recombinant IL-2.

The CTLL-Ns are washed and suspended at a concentration of $10^{-5}$/ml in the culture media. Assays are performed in triplicate, as follows: a serial dilution of the sample aliquot (50 $\mu$l), a 1:10 dilution of the human recombinant IL-2 standard and $10^{-4}$ CTLL-Ns (100 $\mu$l) are placed in microliter wells. The microliter plates are incubated in a humidified 6% $CO_2$ atmosphere at 37° C. for 24 hrs, and the cells are pulsed at the 19th hour with 1 $\mu$Ci/well of methyltritiated thymidine (specific activity 6.7 Ci/mM, New England Nuclear, I. E. Dupont, Boston, Mass.).

The cells are collected onto glass filter paper discs. The discs are placed in scintillation fluid and thymidine uptake is measured by liquid scintillation spectrophotometry. IL-2 inhibitory activity is calculated by modified probit analysis.

The proliferation "maximum" is the tritiated thymidine uptake caused by the amount of exogenous IL-2 activity in the control microliter wells, assessed in quadruplicate for each assay. The proliferation "minimum" is derived from lowest amount of tritiated thymidine uptake caused by the IL-2 inhibitor standard. The probit calculation corrected for minor interassay variations of thymidine uptake in control wells, and permitted interassay comparisons of inhibitor activity among the urine samples. By this treatment of the data, the calculated value of IL-2 inhibitory activity in lyophilized urine samples varies less than 10% from assay to assay. IL-2-IN activity is expressed in units/mg urine creatinine (U/mg u.c.). IL-2-IN activity is less than 0.05 U/mg u.c. in the urine of healthy adults. J. Fleischmann, et al., *Journal of Biological Regulators and Homeostatic Agents*, 4:73, (1990).

Medication Assignments: All patients are treated initially with a total daily dose of 30 mg, which is administered as a single, extended release tablet.

Patient Monitoring: Patients are interviewed and blood pressure measured twice monthly during the first 2 months of therapy, during the first 2 months after a dose escalation, and then once monthly thereafter. The symptom severity score at each interview is based on the patient's experiences during the previous 24 hours.

EXAMPLE 2

In addition to the treatment of patients with interstitial cystitis, patients with the urethral syndrome have been treated with a compound of Formula I, using the titration test and treatment protocol described in U.S. Pat. No. 5,145,859. Similar to the data of Example 1, the positive response to the compounds of the present invention in this limited study supports the hypothesis that the urethralsyndrome and interstitial cystitis are both part of the same disease spectrum, perhaps as variants of reflex sympathetic dystrophy.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See. e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixers, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Preparation 1

Hard gelatin capsules containing the following ingredients are prepared:

| Ingredient | Quantity (mg/capsule) |
| --- | --- |
| Active Ingredient(s) | 30.0 |
| Starch | 305.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
|---|---|
| Active Ingredient(s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
|---|---|
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
|---|---|
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
|---|---|
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
|---|---|
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
|---|---|
| Active Ingredient(s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Qualitity (mg/capsule) |
| --- | --- |
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient(s) | 250.0 mg |
| Isotonic saline | 1000 ml |

Formulation Preparation 10

A topical formulation may be prepared as follows:

| Ingredient | Quantity |
| --- | --- |
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method for the treatment or prevention of interstitial cystitis or urethral syndrome in a mammal which comprise administering to a mammal in need thereof an effective amount of a compound of the formula

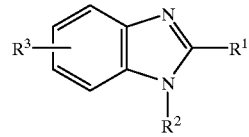

wherein:
$R^1$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-,
any one of which phenyl, naphthyl, heterocyclic, $C_3$–$C_8$ cycloalkyl, or unsaturated heterocyclic groups may be optionally substituted with one, two, or three moieties independently selected from group consisting of heterocyclic-($C_1$–$C_6$ alkylidenyl)-, unsaturated heterocyclic-($C_1$–$C_6$ alkylidenyl)-, hydroxy, halo, $C_1$–$C_6$ alkyl, $C_1$–$C_6$ alkoxy, trifluoromethyl, nitro, amino, cyano, $C_1$–$C_6$ alkylamino, and $C_1$–$C_6$ alkylthio;

$R^2$ is hydrogen, $C_1$–$C_{12}$ alkyl, $C_1$–$C_6$ alkoxy, phenyl, $C_3$–$C_8$ cycloalkyl, naphthyl, heterocyclic, unsaturated heterocyclic, phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-, any one of which phenyl, naphthyl, heterocyclic, $C_3$–$C_8$ cycloalkyl, or unsaturated heterocyclic groups may be optionally substituted with one, two, or three moieties independently selected from group consisting of phenyl-($C_1$–$C_6$ alkylidenyl)-, naphthyl-($C_1$–$C_6$ alkylidenyl)-, heterocyclic-($C_1$–$C_6$ alkylidenyl)-, unsaturated heterocyclic-($C_1$–$C_6$ alkylidenyl)-, phenyl-($C_1$–$C_6$ alkoxy)-, naphthyl-($C_1$–$C_6$ alkoxy)-, heterocyclic-($C_1$–$C_6$ alkoxy)-, or unsaturated heterocyclic-($C_1$–$C_6$ alkoxy)-, hydroxy, halo, $C_1$–$C_6$ alkyl, $C_1$–$C_6$ alkoxy, trifluoromethyl, nitro, amino, cyano, $C_1$–$C_6$ alkylamino, and $C_1$–$C_6$ alkylthio;

$R^3$ is hydrogen, nitro, $C_1$–$C_6$ alkanoyl, amino, $C_1$–$C_6$ alkyl, $C_1$–$C_6$ alkoxy, $C_3$–$C_8$ cycloalkyl, heterocyclic, unsaturated heterocyclic, halo, $C_1$–$C_6$ alkylthio, hydroxy-($C_1$–$C_6$ alkylidenyl)-, hydroxy-($C_1$–$C_6$ alkylidenyl)amino-, $R^4R^5N$-, $R^4R^5N$-($C_1$–$C_6$ alkylidenyl)-, $R^4R^5N$-($C_1$–$C_6$ alkoxy)-, hydroxy-($C_1$–$C_6$ alkyl)-, heterocyclic-($C_1$–$C_6$ alkoxy)-, amino ($C_1$–$C_6$ alkylidenyl)-, or trifluoromethyl, where $R^4$ and $R^5$ are independently selected from the group consisting of $C_1$–$C_6$ alkyl, $C_1$–$C_6$ alkoxy, $C_1$–$C_6$ alkanoyl, aryl, heterocyclic, unsaturated heterocyclic, aryl($C_1$–$C_6$ alkylidenyl)-, heterocyclic ($C_1$–$C_6$ alkylidenyl)-, unsaturated heterocyclic ($C_1$–$C_6$ alkylidenyl)-, and hydrogen or $R^4$ and $R^5$ combine to form $C_3$–$C_8$ cycloalkyl, any one of which alkyl or alkoxy groups may be substituted with one or more halo, amino, or nitro; and any one of which aryl, unsaturated heterocyclic, or heterocyclic groups may be substituted with one, two, or three moieties independently selected from group consisting of hydroxy, halo, $C_1$–$C_6$ alkyl, $C_1$–$C_6$ alkoxy, trifluoromethyl, nitro, amino, cyano, $C_3$–$C_8$ cycloalkyl, $C_1$–$C_6$ alkylamino, and $C_1$–$C_6$ alkylthio;

with the proviso that not more than one of $R^1$ and $R^2$ may be hydrogen;

or a pharmaceutically acceptable salt or solvate thereof.

2. A method as claimed in claim 1 employing employing 1-benzyl-2-(3,4,5-trimethoxyphenyl)-6-[2-(4-morpholinyl)ethoxy]benzimidazole, 1-benzyl-2-(3,4,5-trimethoxyphenyl)-6-[2-(1-piperidinyl)ethoxy]benzimidazole, 1-benzyl-2-(3,4,5-trimethoxyphenyl)-6-[2-(1-pyrroldinyl)ethoxy]benzimidazole, 1-benzyl-2-(3,4,5-trimethoxyphenyl)-6-[2-(1-hexamethyleneiminyl)ethoxy]benzimidazole, 1-benzyl-2-(3,4,5-trimethoxyphenyl)-6-[3-(1-piperidinyl)propoxy]benzimidazole, 1-benzyl-2-(3,4,5-trimethoxyphenyl)-6-[2-[4-(piperidin-1-yl)piperdin-1-yl]ethoxy]benzimidazole, 1-benzyl-2-(3,4,5-trimethoxyphenyl)-6-[2-(4-methyl-1-piperazinyl)ethoxy]benzimidazole, 1-benzyl-2-(3-methylphenyl)-6-[2-(1-pyrrolidinyl)ethoxy]benzimidazole, 1-benzyl-2-(3-methylphenyl)-6-[3-(piperdin-1-yl)propoxy]-benzimidazole, 1-benzyl-2-(3-methylphenyl)-6-[3-(morpholin-4-yl)propoxy)benzimidazole, 1-benzyl-2-(3-methylphenyl)-6-[3-(pyrrolidin-1-yl)propoxy)benzimidazole, 1-benzyl-2-(3-methylphenyl)-6-[3-(hexamethyleneimin-1-yl)propoxy)benzimidazole, 1-benzyl-2-(3 -methylphenyl)-6-[3-heptamethyleneimin-1-yl)propoxy)benzimidazole, 1-benzyl-2-(3-methylphenyl)-6-[2-(4-methyl-piperazin-1-yl)ethoxy]benzimidazole, 1-(2-trifluoromethylbenzyl)-2-(3,4,5-trimethoxyphenyl)-6-[2-(piperidin-1-yl)ethoxy]benzimidazole, 1-(2-trifluoromethylbenzyl)-2-(3,4,5-trimethoxyphenyl)-6-[3-(piperidin-1-yl)propoxy]benzimidazole, 1-(2-trifluoromethylbenzyl)-2-(3,4,5-trimethoxyphenyl)-6-[2-(hexamethyleneimin-1-yl)ethoxy]benzimidazole, 1-(2-trifluoromethylbenzyl)-2-(3,4,5-trimethoxyphenyl)-6-[2-(pyrrolidin-1-yl)ethoxy]benzimidazole, 1-(2-trifluoromethylbenzyl)-2-(3,4,5-trimethoxyphenyl)-6-[2-(morpholin-4-yl)ethoxy]benzimidazole, 1-(2-bromobenzyl)-2-(3,4,5-trimethoxyphenyl)-6-[2-(piperdin-1-yl)ethoxy]benzimidazole, 1-(2-trifluoromethylbenzyl)-2-(3-methylphenyl)-6-[2-(piperidinyl-1-yl)ethoxy]benzimidazole, 1-(2-bromobenzyl)-2-(3-methylphenyl)-6-[2-(piperidinyl-1-yl)ethoxy]benzimidazole, 1-(2-trifluoromethylbenzyl)-2-(3,4dimethylphenyl)-6-[2-piperidin-1-yl)ethoxy]benzimidazole, 1-(2-bromobenzyl)-2-(3,4-dimethylphenyl)-6-[2-(piperidin-1-yl)ethoxy]benzimidazole, or 1-(2-bromobenzyl)-2-(3,5-dimethylphenyl)-6-[2-(piperidin-1-yl)ethoxy]benzimidazole, or a pharmaceutically acceptable salt or solvate thereof.

3. A method as claimed in claim 1 employing employing 1-benzyl-2-(3,4,5-trimethoxyphenyl)-6-[1-methyl-2-(N,N-dimethylamino)]ethoxy]benzimidazole, 1-benzyl-2-(3,4,5-trimethoxyphenyl)-6-[2-(N,N-dimethylamino)ethoxy]benzimidazole, 1-benzyl-2-(3,4,5-trimethoxyphenyl)-6-[3-(N,N-dimethylamino)propoxy]benzimidazole, 1-benzyl-2-(3,4,5-timethoxyphenyl)-6-[2-(N,N-diisopropylamino)ethoxy]benzimidazole, 1-benzyl-2-(3-methylphenyl)-6-[2-(N,N-dimethylamino)ethoxy]benzimidazole, 1-benzyl-2-(3-methylphenyl)-6-[2-(N,N-diethylamino)ethoxy]-benzimidazole, 1-benzyl-2-(3-methylphenyl)-6 -[3-(N,N-dimethylamino)propoxy]benzimidazole, 1-benzyl-2-(3-methylphenyl)-6-[2-(N,N-isopropylamino)ethoxy]benzimidazole, 1-benzyl-2-(3-methylphenyl)-6-[2-(N,N-dibenzylamino)ethoxy]benzimidazole, 1-benzyl-2-(3-methylphenyl)-6-[3-(N,N-dimethylamino)propoxy]benzimidazole, 1-benzyl-2-(3-methylphenyl)-6-[2-(N,N-dimethylamino)propoxy]-benzimidazole, 1-(2-trifluoromethylbenzyl)-2-(3,4,5-trimethoxyphenyl)-6-[2-(N,N-dimethylamino)propoxy]-benzimidazole, 1-(2-trifluoromethylbenzyl)-2-(3,4,5-trimethoxyphenyl)-6-[2-(N,N-dimethylamino)ethoxy]-benzimidazole, 1-(2-trifluoromethylbenzyl)-2-(3,4,5-trimethoxyphenyl)-6-[3-(N,N-dimethylamino)propoxy]-benzimidazole, 1-(2-trifluoromethylbenzyl)-2-(3,4,5-trimethoxyphenyl)-6-[2-(N,N-diisopropylamino)ethoxy]benzimidazole, 1-(2-bromobenzyl)-2-(3,4,5-trimethoxyphenyl-6-[2-(N,N-dimethylamino)propoxy]benzimidazole, 1-(2-bromobenzyl)-2-(3,4,5-trimethoxyphenyl)-6-[2-(N,N-dimethylamino)ethoxy]benzimidazole, 1-(2-bromobenzyl)-2-(3,4,5-trimethoxyphenyl)-6-[3-(N,N-dimethylamino)propoxy]benzimidazole, 1-(2-bromobenzyl)-2-(3,4,5-trimethoxyphenyl)-6-[2-(N,N-diisopropylamino)ethoxy]benzimidazole, 1-(2-trifluoromethylbenzyl)-2-(3-methylphenyl)-6-[2-(N,N-dimethylamino)ethoxy]benzimidazole, 1-(2-trifluoromethylbenzyl)-2-(3-methylphenyl)-6-[3-(N,N-dimethylamino)propoxy]benzimidazole, 1-(2-bromobenzyl)-2-(3-methylphenyl)-6-

[2-(N,N-dimethylamino)ethoxy]benzimidazole, 1-(2-bromobenzyl)-2-(3-methylphenyl)-6-[3-(N,N-dimethylamino)propoxy]benzimidazole, 1-(2-trifluoromethylbenzyl)-2-(3,4-dimethylphenyl)-6-[2-(N,N-dimethylamino)ethoxy]benzimidazole, 1-(2-trifluoromethylbenzyl)-2-(3,4-dimethylphenyl)-6-[2-(N,N-diisopropylamino)ethoxy]benzimidazole, 1-(2-bromobenzyl)-2-(3,4-dimethylphenyl)-6-[2-(N,N-dimethylamino)ethoxy]benzimidazole, 1-(2-bromobenzyl)-2-(3,4-dimethylphenyl)-6-[2-(N,N-diisopropylamino)ethoxy]benzimidazole, 1-(2-bromobenzyl)-2-(3,4-dimethylphenyl)-6-[1-methyl-2-(N,N-dimethylamino)ethoxy]benzimidazole, 1-(2-bromobenzyl)-2-(3,5-dimethylphenyl)-6-[2-(N,N-dimethylamino)ethoxy]benzimidazole, 1-(2-bromobenzyl)-2-(3,5-dimethylphenyl)-6-[1-methyl-2-(N,N-dimethylamino)ethoxy]benzimidazole, 1-(2-bromobenzyl)-2-(3,5-dimethylphenyl)-6-[2-(N,N-diisopropylamino)ethoxy]benzimidazole, or 1-(2-bromobenzyl)-2-(3,5-dimethylphenyl)-6-[3-(N,N-dimethylamino)propoxy]benzimidazole, or a pharmaceutically acceptable salt or solvate thereof.

* * * * *

UNITED STATES PATENT AND TRADEMARK OFFICE
CERTIFICATE OF CORRECTION

PATENT NO. : 6,025,379

DATED : February 15, 2000

INVENTOR(S) : Smriti Iyengar, et al.

It is certified that an error appears in the above-identified patent and that said Letters Patent is hereby corrected as shown below:

Column 60, line 36, delete the term "timethoxyphenyl" and replace it with --trimethoxyphenyl--.

Signed and Sealed this

Twenty-fourth Day of April, 2001

Attest:

NICHOLAS P. GODICI

Attesting Officer

*Acting Director of the United States Patent and Trademark Office*